(12) United States Patent
Bhimavarapu et al.

(10) Patent No.: US 12,702,605 B2
(45) Date of Patent: Aug. 11, 2026

(54) PATIENT SUPPORT SYSTEMS AND METHODS FOR ASSISTING CAREGIVERS WITH PATIENT CARE

(71) Applicant: Stryker Corporation, Kalamazoo, MI (US)

(72) Inventors: Krishna S. Bhimavarapu, Kalamazoo, MI (US); Daniel Brosnan, Kalamazoo, MI (US); Aaron Douglas Furman, Kalamazoo, MI (US); Annie Desaulniers, Bothell, WA (US); Ming Chen, Ann Arbor, MI (US)

(73) Assignee: Stryker Corporation, Portage, MI (US)

( * ) Notice: Subject to any disclaimer, the term of this patent is extended or adjusted under 35 U.S.C. 154(b) by 218 days.

(21) Appl. No.: 17/836,384

(22) Filed: Jun. 9, 2022

(65) Prior Publication Data

US 2022/0304875 A1 Sep. 29, 2022

Related U.S. Application Data

(63) Continuation of application No. 16/020,052, filed on Jun. 27, 2018, now Pat. No. 11,382,812.

(Continued)

(51) Int. Cl.

*A61G 7/018* (2006.01)
*A61G 7/00* (2006.01)

(Continued)

(52) U.S. Cl.

CPC ........... *A61G 7/018* (2013.01); *A61G 7/0005* (2013.01); *A61G 7/0506* (2013.01);

(Continued)

(58) Field of Classification Search

CPC ...... A61G 7/018; A61G 7/005; A61G 7/0506; A61G 7/0507; A61G 7/10; A61G 7/001;

(Continued)

(56) References Cited

U.S. PATENT DOCUMENTS

| | | | |
|---|---|---|---|
| 5,113,214 | A | 5/1992 | Nagata et al. |
| 5,276,432 | A | 1/1994 | Travis |

(Continued)

FOREIGN PATENT DOCUMENTS

| | | | |
|---|---|---|---|
| CN | 101789230 | A | 7/2010 |
| DE | 19505162 | C1 | 3/1996 |

(Continued)

OTHER PUBLICATIONS

Apple, "Adjust the Brightness on you iPhone, IPad, or IPod Touch", https://support.apple.com/en-us/HT202613, 2018, 2 pages.

(Continued)

*Primary Examiner* — Justin C Mikowski
*Assistant Examiner* — Amanda L Bailey
(74) *Attorney, Agent, or Firm* — Howard & Howard Attorneys PLLC

(57) ABSTRACT

A patient support system for providing improved guidance tools with respect to a patient support apparatus. A user interface is configured to receive inputs from a user, and an information output device is configured to provide instructions to the user. The user interface and the information output device may be on a touchscreen display. The user inputs may include a search query. A controller may be adapted to determine search results corresponding to operational functions of the patient support apparatus responsive to the search query and to provide said search results to the user with the information output device. The user input may include shorthand commands corresponding to operational functions of the patient support apparatus. The user interface may include a voice actuation device configured to receive voice actuation commands from a user.

17 Claims, 6 Drawing Sheets

Related U.S. Application Data

(60) Provisional application No. 62/525,359, filed on Jun. 27, 2017.

(51) Int. Cl.

*A61G 7/012* (2006.01)
*A61G 7/05* (2006.01)
*A61G 7/053* (2006.01)
*A61G 7/057* (2006.01)
*A61G 7/10* (2006.01)
*G06F 16/248* (2019.01)
*G16H 20/30* (2018.01)
*G16H 40/63* (2018.01)

(52) U.S. Cl.

CPC ............. *A61G 7/0507* (2013.01); *A61G 7/10* (2013.01); *G06F 16/248* (2019.01); *G16H 20/30* (2018.01); *G16H 40/63* (2018.01); *A61G 7/001* (2013.01); *A61G 7/012* (2013.01); *A61G 7/053* (2013.01); *A61G 7/05769* (2013.01); *A61G 2203/12* (2013.01); *A61G 2203/16* (2013.01); *A61G 2203/18* (2013.01); *A61G 2203/20* (2013.01); *A61G 2203/70* (2013.01)

(58) Field of Classification Search

CPC .... A61G 7/012; A61G 7/053; A61G 7/05769; A61G 2203/10; A61G 2203/12; A61G 2203/16; A61G 2203/18; A61G 2203/20; A61G 2203/70; A61B 6/04; A61B 6/0407; A61B 6/0428

See application file for complete search history.

(56) References Cited

U.S. PATENT DOCUMENTS 5,434,621 A 7/1995 Yu
5,640,953 A 6/1997 Bishop et al.
5,645,667 A 7/1997 Kusen
5,664,270 A 9/1997 Bell et al.
5,864,105 A * 1/1999 Andrews .............. B60N 2/0228 200/5 R
5,971,913 A 10/1999 Newkirk et al.
6,320,510 B2 11/2001 Menkedick et al.
6,340,977 B1 1/2002 Lui et al.
6,362,725 B1 3/2002 Ulrich et al.
6,702,314 B1 3/2004 Crose
6,876,303 B2 4/2005 Reeder et al.
6,948,592 B2 9/2005 Kavounas
7,154,397 B2 12/2006 Zerhusen et al.
7,296,312 B2 11/2007 Menkedick et al.
7,319,386 B2 1/2008 Collins, Jr. et al.
7,336,187 B2 2/2008 Hubbard, Jr. et al.
7,389,552 B1 6/2008 Reed et al.
7,443,302 B2 10/2008 Reeder et al.
7,472,439 B2 1/2009 Lemire et al.
7,487,562 B2 2/2009 Frondorf et al.
7,490,021 B2 2/2009 Holland et al.
7,570,152 B2 8/2009 Smith et al.
7,690,059 B2 4/2010 Lemire et al.
7,747,644 B1 6/2010 Reihl et al.
7,888,901 B2 2/2011 Larson et al.
7,895,519 B1 2/2011 Allegrezza et al.
8,069,157 B2 11/2011 Jam
8,117,701 B2 2/2012 Bobey et al.
8,121,856 B2 2/2012 Huster et al.
8,143,846 B2 3/2012 Herman et al.
8,165,908 B2 4/2012 Bolle et al.
8,209,608 B1 6/2012 Linyard et al.
8,266,742 B2 9/2012 Andrienko
8,308,237 B2 11/2012 Kunou
8,319,633 B2 11/2012 Becker et al.
8,334,779 B2 12/2012 Zerhusen et al.
8,341,777 B2 1/2013 Hensley et al.
8,344,860 B2 1/2013 Collins, Jr. et al.
8,410,943 B2 4/2013 Metz et al.
8,413,270 B2 4/2013 Turner et al.
8,413,271 B2 4/2013 Blanchard et al.
8,432,287 B2 4/2013 O'Keefe et al.
8,442,738 B2 5/2013 Patmore
8,464,380 B2 6/2013 Bobey et al.
8,525,682 B2 9/2013 Dixon et al.
8,544,126 B2 10/2013 Elliott et al.
8,552,880 B2 10/2013 Kopp et al.
8,596,716 B1 * 12/2013 Caruso .................... G06F 3/041 297/217.3
8,604,917 B2 12/2013 Collins et al.
8,641,301 B2 2/2014 Yang et al.
8,650,682 B2 2/2014 Herman
8,674,839 B2 3/2014 Zerhusen et al.
8,716,941 B2 5/2014 Kim
8,756,078 B2 6/2014 Collins, Jr. et al.
8,768,520 B2 7/2014 Dexman et al.
8,789,102 B2 7/2014 Pickelsimer et al.
8,847,756 B2 9/2014 Tallent et al.
8,868,542 B2 10/2014 Kimball et al.
8,870,812 B2 10/2014 Alberti et al.
8,896,524 B2 11/2014 Birnbaum et al.
8,923,994 B2 12/2014 Laikari et al.
8,924,218 B2 12/2014 Corpier et al.
8,926,535 B2 1/2015 Rawls-Meehan
8,984,685 B2 3/2015 Robertson et al.
9,001,038 B2 4/2015 Kasahara
9,032,510 B2 5/2015 Sampathkumaran et al.
9,038,217 B2 5/2015 Elliot et al.
9,088,282 B2 7/2015 Holenarsipur et al.
9,126,571 B2 9/2015 Lemire et al.
9,138,173 B2 9/2015 Penninger et al.
9,173,792 B2 11/2015 Goffer
9,204,823 B2 12/2015 Derenne et al.
9,220,650 B2 12/2015 Bobey et al.
9,230,421 B2 1/2016 Reeder et al.
9,233,033 B2 1/2016 Valentino et al.
9,259,369 B2 2/2016 Derenne et al.
9,262,876 B2 2/2016 Wood et al.
9,320,664 B2 4/2016 Newkirk et al.
9,342,677 B2 5/2016 Ali et al.
9,381,125 B2 7/2016 Herbst et al.
9,424,699 B2 8/2016 Kusens et al.
9,456,938 B2 10/2016 Blickensderfer et al.
9,463,126 B2 10/2016 Zerhusen et al.
9,466,163 B2 10/2016 Kusens et al.
9,486,084 B2 11/2016 Connell et al.
9,569,591 B2 2/2017 Vanderpohl, III
9,593,833 B2 3/2017 McMannon et al.
9,655,798 B2 5/2017 Zerhusen et al.
9,691,206 B2 6/2017 Kusens et al.
9,774,991 B2 9/2017 Kusens
9,814,410 B2 11/2017 Kostic et al.
9,838,849 B2 12/2017 Kusens
9,844,275 B2 12/2017 Nunn et al.
9,849,051 B2 12/2017 Newkirk et al.
9,858,741 B2 1/2018 Kusens et al.
9,892,310 B2 2/2018 Kusens et al.
9,892,311 B2 2/2018 Kusens et al.
9,916,649 B1 3/2018 Kusens
9,934,427 B2 4/2018 Derenne et al.
9,940,810 B2 4/2018 Derenne et al.
9,984,521 B1 5/2018 Kusens et al.
9,998,857 B2 6/2018 Kusens
9,999,555 B2 6/2018 Magill et al.
10,004,654 B2 6/2018 Zerhusen et al.
10,034,979 B2 7/2018 Bechtel et al.
10,052,249 B2 8/2018 Elliott et al.
10,098,796 B2 10/2018 Valentino et al.
10,136,841 B2 11/2018 Alghazi
10,172,752 B2 1/2019 Goffer
10,188,569 B2 1/2019 Elku et al.
10,410,500 B2 9/2019 Derenne et al.
10,811,136 B2 10/2020 Bhimavarapu et al.
10,905,609 B2 2/2021 Childs et al.
11,096,850 B2 8/2021 Bhimavarapu et al.

(56) References Cited

U.S. PATENT DOCUMENTS 11,202,729 B2 12/2021 Desaulniers
11,337,872 B2 5/2022 Bhimavarapu et al.
2002/0014951 A1 2/2002 Kramer et al.
2003/0052787 A1 3/2003 Zerhusen et al.
2003/0183427 A1 10/2003 Tojo et al.
2004/0083394 A1 4/2004 Brebner et al.
2006/0077186 A1 4/2006 Park et al.
2006/0102392 A1 5/2006 Johnson et al.
2006/0117482 A1* 6/2006 Branson ............. A61G 7/05769 5/600
2007/0163045 A1 7/2007 Becker et al.
2007/0174965 A1* 8/2007 Lemire ................ A61G 7/0528 5/630
2007/0219950 A1 9/2007 Crawford
2008/0141459 A1 6/2008 Hamberg et al.
2008/0172789 A1* 7/2008 Elliot .................. A61G 7/0527 5/616
2008/0235872 A1 10/2008 Newkirk et al.
2009/0153370 A1 6/2009 Cooper et al.
2009/0210110 A1* 8/2009 Dybalski ............... H04L 67/125 345/173
2009/0222184 A1* 9/2009 Bhai ........................ A61G 7/08 5/81.1 R
2009/0228825 A1* 9/2009 Van Os .................. G06F 16/14 715/780
2010/0039414 A1 2/2010 Bell
2010/0169841 A1* 7/2010 Singh .................. G06F 3/04883 345/173
2010/0212087 A1 8/2010 Leib et al.
2011/0080421 A1 4/2011 Capener
2011/0162067 A1 6/2011 Shuart et al.
2011/0169653 A1 7/2011 Wang et al.
2012/0023670 A1 2/2012 Zerhusen et al.
2012/0089419 A1 4/2012 Huster et al.
2012/0137436 A1 6/2012 Andrienko
2012/0215360 A1* 8/2012 Zerhusen ............... A61G 7/018 700/275
2012/0239173 A1 9/2012 Laikari et al.
2013/0138452 A1 5/2013 Cork et al.
2013/0142367 A1 6/2013 Berry et al.
2013/0227787 A1 9/2013 Herbst et al.
2013/0238991 A1 9/2013 Jung et al.
2013/0300867 A1 11/2013 Yoder
2013/0318716 A1 12/2013 Vanderpohl, III
2014/0076644 A1 3/2014 Derenne et al.
2014/0259410 A1 9/2014 Zerhusen et al.
2014/0265181 A1 9/2014 Lambarth et al.
2014/0297327 A1 10/2014 Heil et al.
2014/0313700 A1 10/2014 Connell et al.
2014/0342330 A1 11/2014 Freeman et al.
2015/0002393 A1 1/2015 Cohen et al.
2015/0060162 A1 3/2015 Goffer
2015/0077534 A1 3/2015 Derenne et al.
2015/0109442 A1 4/2015 Derenne et al.
2015/0154002 A1 6/2015 Weinstein et al.
2015/0250669 A1 9/2015 Elliott et al.
2015/0317068 A1 11/2015 Marka et al.
2016/0012218 A1 1/2016 Perna et al.
2016/0022039 A1 1/2016 Paul et al.
2016/0038361 A1 2/2016 Bhimavarapu et al.
2016/0045382 A1 2/2016 Goffer
2016/0049028 A1 2/2016 Kusens et al.
2016/0050217 A1 2/2016 Mare et al.
2016/0065909 A1 3/2016 Derenne et al.
2016/0095774 A1 4/2016 Bobey et al.
2016/0140307 A1 5/2016 Brosnan et al.
2016/0180668 A1 6/2016 Kusens et al.
2016/0180728 A1 6/2016 Clark et al.
2016/0183864 A1 6/2016 Kusens et al.
2016/0193095 A1 7/2016 Roussy et al.
2016/0199240 A1 7/2016 Newkirk et al.
2016/0247342 A1 8/2016 Kusens et al.
2016/0250088 A1* 9/2016 Williamson ........... A61G 7/002 5/617
2016/0274789 A1* 9/2016 Park ...................... G06F 3/0486
2016/0296396 A1 10/2016 Kolar et al.
2016/0324705 A1 11/2016 Bach Castillo
2016/0338891 A1 11/2016 Agdeppa et al.
2016/0366327 A1 12/2016 Kusens
2016/0367420 A1 12/2016 Zerhusen et al.
2016/0371786 A1 12/2016 Kusens et al.
2017/0027789 A1 2/2017 St.John et al.
2017/0049642 A9 2/2017 Valentino et al.
2017/0055113 A1 2/2017 Kusens
2017/0076526 A1 3/2017 Kusens et al.
2017/0094477 A1 3/2017 Kusens et al.
2017/0097800 A1 4/2017 Vanderpohl, III
2017/0098048 A1 4/2017 Brosnan et al.
2017/0109770 A1 4/2017 Kusens et al.
2017/0111770 A1 4/2017 Kusens
2017/0116790 A1 4/2017 Kusens et al.
2017/0124844 A1 5/2017 Huster et al.
2017/0128296 A1 5/2017 Kostic et al.
2017/0143565 A1 5/2017 Childs et al.
2017/0193177 A1 7/2017 Kusens
2017/0193180 A1 7/2017 Kusens et al.
2017/0193279 A1 7/2017 Kusens et al.
2017/0193772 A1 7/2017 Kusens et al.
2017/0195637 A1 7/2017 Kusens et al.
2017/0213445 A1 7/2017 Kusens
2017/0224562 A1 8/2017 Zerhusen et al.
2017/0229009 A1 8/2017 Foster et al.
2017/0259811 A1 9/2017 Coulter et al.
2017/0281440 A1 10/2017 Puvogel et al.
2017/0329872 A1 11/2017 Dispensa et al.
2017/0352212 A1 12/2017 Kusens et al.
2018/0017945 A1 1/2018 Sidhu et al.
2018/0039743 A1 2/2018 Dixon et al.
2018/0040091 A1 2/2018 Kusens
2018/0041864 A1 2/2018 Kusens
2018/0055418 A1 3/2018 Kostic et al.
2018/0056985 A1 3/2018 Coulter et al.
2018/0084390 A1 3/2018 Kusens
2018/0096550 A1 4/2018 Kusens et al.
2018/0110445 A1 4/2018 Bhimavarapu et al.
2018/0114053 A1 4/2018 Kusens et al.
2018/0137340 A1 5/2018 Kusens et al.
2018/0151010 A1 5/2018 Kusens et al.
2018/0161225 A1 6/2018 Zerhusen et al.
2018/0167816 A1 6/2018 Kusens et al.
2018/0184984 A1 7/2018 Zerhusen et al.
2018/0189946 A1 7/2018 Kusens et al.
2018/0211464 A1 7/2018 Kusens et al.
2018/0218489 A1 8/2018 Kusens
2018/0250177 A1 9/2018 Magill et al.
2018/0271286 A1 9/2018 Jacobs et al.
2018/0271287 A1 9/2018 Jacobs et al.
2018/0303687 A1 10/2018 Moreno et al.
2018/0369035 A1 12/2018 Bhimavarapu et al.
2018/0369037 A1 12/2018 Desaulniers et al.
2018/0369038 A1 12/2018 Bhimavarapu et al.
2018/0369039 A1 12/2018 Bhimavarapu et al.
2018/0374573 A1 12/2018 Bhimavarapu et al.
2018/0374577 A1 12/2018 Bhimavarapu
2019/0008708 A1 1/2019 Moreno et al.
2019/0024882 A1 1/2019 Jonsson et al.
2019/0046373 A1 2/2019 Coulter et al.

FOREIGN PATENT DOCUMENTS

EP 0727298 A1 8/1996
EP 0727298 B1 8/1999
EP 2489341 A2 8/2012
EP 2531159 A2 12/2012
EP 2619724 A2 7/2013
EP 2918255 A1 9/2015
JP 2003140631 A 5/2003
KR 20130076922 A 7/2013
WO 0101913 A1 1/2001
WO 2006089399 A2 8/2006
WO 2011097569 A2 8/2011
WO 2012040554 A2 3/2012
WO 2014021873 A1 2/2014

(56) References Cited

FOREIGN PATENT DOCUMENTS

| | | | | |
|---|---|---|---|---|
| WO | WO-2014076141 | A2 * | 5/2014 | ............ A61B 34/25 |
| WO | 2015148578 | A2 | 10/2015 | |
| WO | 2015157402 | A1 | 10/2015 | |
| WO | 2015171365 | A1 | 11/2015 | |
| WO | 2016123595 | A1 | 8/2016 | |
| WO | 2016196403 | A1 | 12/2016 | |
| WO | 2016200556 | A1 | 12/2016 | |
| WO | 2017027427 | A1 | 2/2017 | |
| WO | 2017031111 | A1 | 2/2017 | |
| WO | 2017061471 | A1 | 4/2017 | |
| WO | 2017124056 | A1 | 7/2017 | |
| WO | 2017201513 | A1 | 11/2017 | |
| WO | 2018026979 | A1 | 2/2018 | |
| WO | 2018154819 | A1 | 8/2018 | |
| WO | 2018203476 | A1 | 11/2018 | |
| WO | 2018216387 | A1 | 11/2018 | |

OTHER PUBLICATIONS

Astral Healthcare, "Opthalmology Day Surgery Chair Webpage", Apr. 2018, http://astralhealthcare.com/?product=opthalmology-day-surgery-chair, 6 pages.

Campbell, Mikey, "Apple Expected to Replace Touch ID With Two-Step Facial, Fingerprint Bio-Recognition Tech", Apple Insider, Jan. 21, 2017, http://iphone.appleinsider.com/articles/17/01/21/apple-expected-to-replace-touch-id-with-two-step-facial-fingerprint-bio-recognition-tech, 4 pages.

Doge Medical, "DOC Classic—DOC Surgery Chairs Webpage", 2014, 2 pages, https://web.archive.org/web/20140214203605/http://www.dogemedical.com/pages/en/products/surgery-chairs/doc-classic.php?lang=EN.

English language abstract and machine-assisted English translation for CN 101789230 extracted from espacenet.com database on Aug. 30, 2018, 31 pages.

English language abstract and machine-assisted English translation for JP 2003-140631 extracted from espacenet.com database on Aug. 30, 2018, 19 pages.

English language abstract and machine-assisted English translation for KR 2013-0076922 A extracted from espacenet.com database on Aug. 16, 2018, 8 pages.

English language abstract and machine-assisted English translation for WO 2017/061471 extracted from espacenet.com database on Mar. 25, 2019, 26 pages.

English language abstract and machine-assisted English translation for WO 2018/154819 extracted from espacenet.com database on Mar. 25, 2019, 35 pages.

English language abstract and machine-assisted English translation for WO 2018/203476 extracted from espacenet.com database on Mar. 25, 2019, 37 pages.

English language abstract and machine-assisted English translation for WO 2018/216387 extracted from espacenet.com database on Mar. 25, 2019, 43 pages.

English language abstract for DE 195 05 162 C1 extracted from espacenet.com database on Aug. 16, 2018, 1 page.

English language abstract for EP 0 727 298 A1 extracted from espacenet.com database on Aug. 16, 2018, 1 page.

English language abstract for EP 0 727 298 B1 extracted from espacenet.com database on Aug. 16, 2018, 1 page.

Hall, Stephen, "Nest's 3rd Generation Thermostat Gets Some New Views for Its Farsight Feature", 9 to 5 Google, Jun. 14, 2016, https://9to5google.com/2016/06/14/nest-3rd-gen-thermostat-views-farsight/, 4 pages.

Hill-Rom, "Centrella Smart+Bed Brochure" 2017, 11 pages.

Imore, "How to Use Night Shift on your iPhone or iPad", video also found at https://www.imore.com/night-shift, Nov. 1, 2017, 12 pages.

Recliners.LA "Stellar 550 Large Lift Chair Recliner Webpage", Apr. 2018, https://www.recliners.la/products/ultra-comfort-stellar-550-large-lift-chair, 4 pages.

Stryker Medical, "InTouch Critical Care Bed Operations Manual", Aug. 2014, 125 pages.

Stryker, "Epic II Critical Care Bed Model 2030 Operations Manual", 2030-309-001, Rev A, https://techweb.stryker.com/Critical_Care/2030/0711/operation/2030-309-001A.pdf, Nov. 2007, 56 pages.

Stryker, "InTouch Critical Care Bed Model FL27 (2130/2140) Operations Manual—Optional Pendant Control", 2130-009-001 Rev C, Apr. 2008, p. 25.

Supportec-Trade, "Portfolilio Webpage", 2017, https://supportec-trade.nl/en, 2 pages.

U.S. Appl. No. 16/019,973, filed Jun. 27, 2018, 90 pages.

U.S. Appl. No. 16/019,986, filed Jun. 27, 2018, 57 pages.

U.S. Appl. No. 16/020,003, filed Jun. 27, 2018, 37 pages.

U.S. Appl. No. 16/020,052, filed Jun. 27, 2018, 48 pages.

U.S. Appl. No. 16/020,068, filed Jun. 27, 2018, 125 pages.

U.S. Appl. No. 16/020,085, filed Jun. 27, 2018, 67 pages.

U.S. Appl. No. 62/525,359, filed Jun. 27, 2017.

U.S. Appl. No. 62/525,363, filed Jun. 27, 2017.

U.S. Appl. No. 62/525,368, filed Jun. 27, 2017.

U.S. Appl. No. 62/525,373, filed Jun. 27, 2017.

U.S. Appl. No. 62/525,377, filed Jun. 27, 2017.

Youtube, "Memory Seat Escape Video", Nov. 4, 2013, https://www.youtube.com/watch?v=xlghNmAK-7A, 1 page.

Youtube, "Microsoft HoloLens: Partner Spotlight with Stryker Communications Video", Feb. 21, 2017, https://www.youtube.com/watch?v=FTPxUGRGpnA, 3 pages.

Youtube, "Umano Medical Med Surg Bed: The Next Generation of Medical Bed (Canadian Version) Video", https://www.bing.com/videos/search?q=umano+ook+snow&&view=detail&mid=2407A16C09D0734591912407A16C09D073459191&rvsmid=FFCD5876C49E791738DFFFCD5876C49E791738DF&FORM=VDRVRV, Apr. 14, 2015, 3 pages.

* cited by examiner

PATIENT SUPPORT SYSTEMS AND METHODS FOR ASSISTING CAREGIVERS WITH PATIENT CARE

CROSS REFERENCE TO RELATED APPLICATIONS

This application is a Continuation of U.S. patent application Ser. No. 16/020,052, filed on Jun. 27, 2018, which claims priority to and the benefit of U.S. Provisional Patent Application No. 62/525,359, filed on Jun. 27, 2017, the disclosures of each of which are hereby incorporated by reference in their entirety.

BACKGROUND

Patient support systems facilitate care of patients in a health care setting. Patient support systems comprise patient support apparatuses such as, for example, hospital beds, stretchers, cots, tables, wheelchairs, and chairs. A conventional patient support apparatus comprises a base and a patient support surface upon which the patient is supported. Often, the patient support apparatus has one or more powered devices to perform one or more functions on the patient support apparatus. These functions can include lifting and lowering the patient support surface, raising a patient from a slouched position, turning a patient, centering a patient, extending a length or width of the patient support apparatus, and the like. When a user such as a caregiver wishes to operate a powered device to perform a function, the user actuates a user interface. Conventional user interfaces may comprise a panel of buttons configured to selectively operate the various operational functions of the patient support apparatus.

The number and complexity of the operational functions integrated into the patient support apparatus continue to increase, and the evolution of user interfaces has been commensurate. Yet increasingly advanced user interfaces are inherently more difficult to operate, particularly to users not familiar with their operation. Users experiencing difficulty with operating the user interface lack adequate guidance tools. Therefore, a need exists in the art for a patient support system providing improved tools to control the operations of the patient support apparatus. There is a further need for the guidance tools to be easily and readily accessible through the user interface of the patient support apparatus.

BRIEF DESCRIPTION OF THE DRAWINGS

Advantages of the present disclosure will be readily appreciated as the same becomes better understood by reference to the following detailed description when considered in connection with the accompanying drawings.

DETAILED DESCRIPTION

Figure 1:
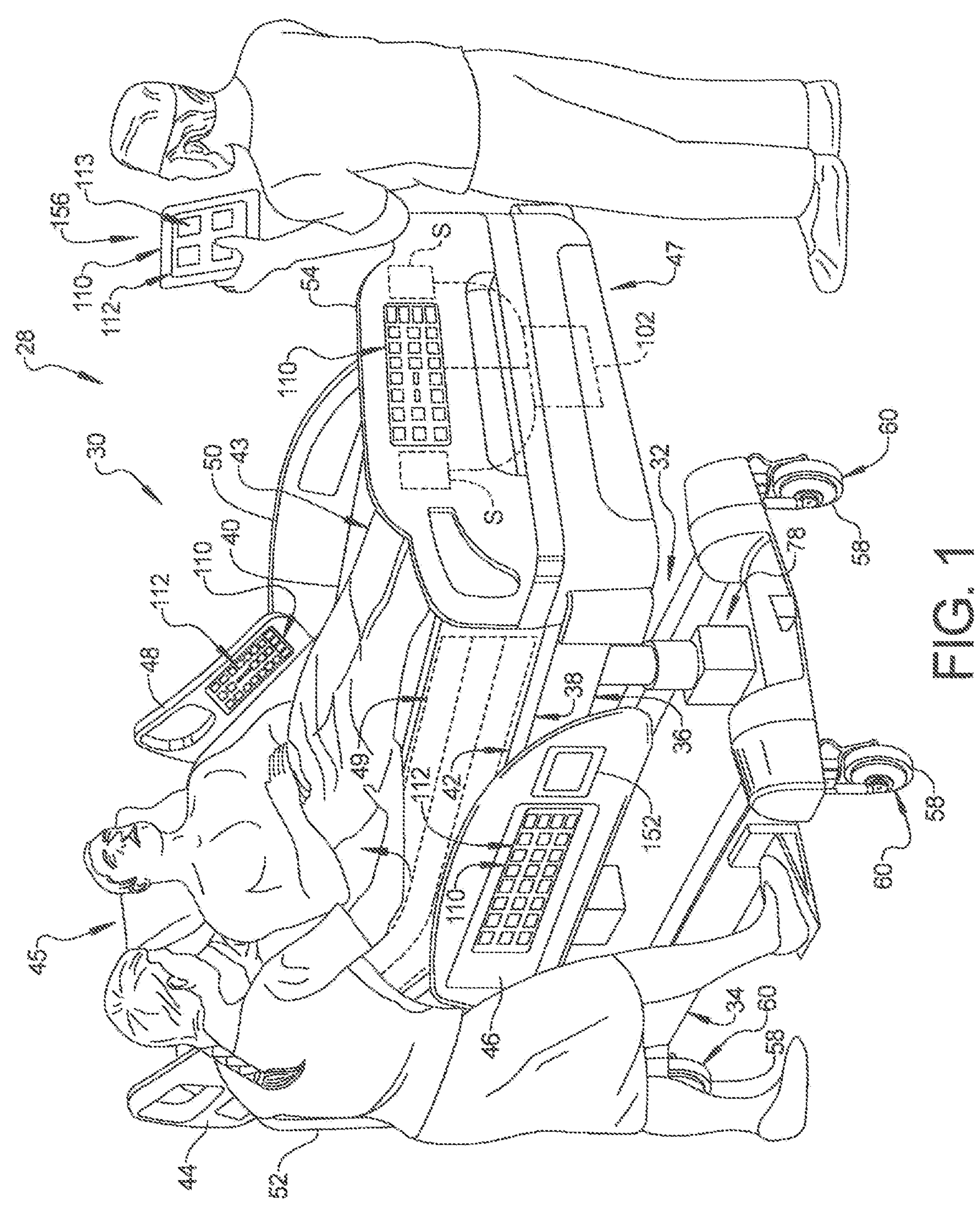
FIG. 1 is perspective view of a patient support apparatus.

FIG. 1 shows a patient support system 28 comprising a patient support apparatus 30 for supporting a patient. The patient support apparatus 30 illustrated in FIG. 1 comprises a hospital bed. In other embodiments, the patient support apparatus 30 may comprise a stretcher, cot, table, wheelchair, chair, or similar apparatus utilized in the care of a patient.

A support structure 32 provides support for the patient. The support structure 32 illustrated in FIG. 1 comprises a base 34 and an intermediate frame 36. The intermediate frame 36 is spaced above the base 34. The support structure 32 also comprises a patient support deck 38 disposed on the intermediate frame 36. The patient support deck 38 comprises several sections, some of which pivot or otherwise articulate relative to the intermediate frame 36, such as a fowler section, a seat section, a thigh section, and a foot section. The patient support deck 38 provides a patient support surface 42 upon which the patient is supported.

A mattress 40 is disposed on the patient support deck 38. The mattress 40 comprises a secondary patient support surface 43 upon which the patient is supported. The base 34, intermediate frame 36, patient support deck 38, and patient support surfaces 42, 43 each have a head end 45 and a foot end 47 corresponding to a designated placement of the patient's head and feet on the patient support apparatus 30. The construction of the support structure 32 may take on any known or conventional design, and is not limited to that specifically set forth above. In addition, the mattress 40 may be omitted in certain embodiments, such that the patient rests directly on the patient support surface 42.

Side rails 44, 46, 48, 50 are coupled to the intermediate frame 36 and thereby supported by the base 34. A first side rail 44 is positioned at a right head end of the intermediate frame 36. A second side rail 46 is positioned at a right foot end of the intermediate frame 36. A third side rail 48 is positioned at a left head end of the intermediate frame 36. A fourth side rail 50 is positioned at a left foot end of the intermediate frame 36. If the patient support apparatus 30 is a stretcher or a cot, there may be fewer side rails. The side rails 44, 46, 48, 50 are movable between a raised position in which they block ingress into and egress out of the patient support apparatus 30, one or more intermediate positions, and a lowered position in which they are not an obstacle to such ingress and egress. In still other configurations, the patient support apparatus 30 may not include any side rails.

A headboard 52 and a footboard 54 are coupled to the intermediate frame 36. In other embodiments, when the headboard 52 and the footboard 54 are included, the headboard 52 and the footboard 54 may be coupled to other locations on the patient support apparatus 30, such as the base 34. In still other embodiments, the patient support apparatus 30 does not include the headboard 52 and/or the footboard 54.

Wheels 58 are coupled to the base 34 to facilitate transport over floor surfaces. The wheels 58 are arranged in each of four quadrants of the base 34 adjacent to corners of the base 34. In the embodiment shown, the wheels 58 are caster wheels able to rotate and swivel relative to the support structure 32 during transport. Each of the wheels 58 forms part of a caster assembly 60. Each caster assembly 60 is mounted to the base 34. It should be understood that various configurations of the caster assemblies 60 are contemplated. In addition, in some embodiments, the wheels 58 are not caster wheels and may be non-steerable, steerable, non-powered, powered, or combinations thereof. Additional wheels are also contemplated. For example, the patient support apparatus 30 may comprise four non-powered, non-steerable wheels, along with one or more powered wheels. In some cases, the patient support apparatus 30 may not include any wheels.

Figure 2:
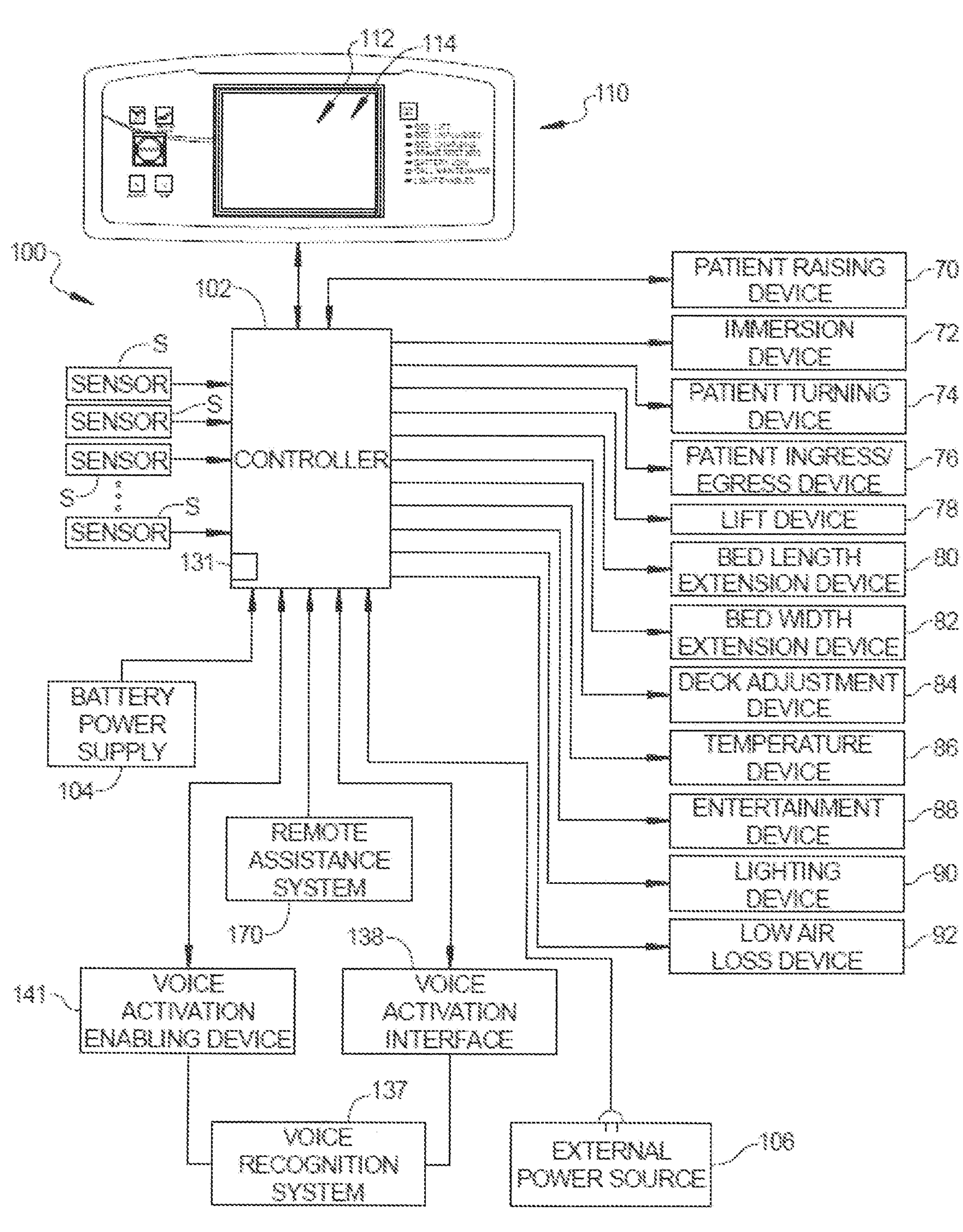
FIG. 2 is a schematic view of a control system.

Referring to FIG. 2, the patient support system 28 may comprise one or more operational devices 70, 72, 74, 76, 78, 90, 82, 84, 86, 88, 90, 92 of the patient support apparatus 30, each configured to perform one or more predetermined operational functions. The operational devices 70-92 utilize one or more components that require electricity. The operational devices 70-92 may comprise powered devices for adjustment, such as a patient raising device 70, an immersion device 72, a patient turning device 74, a patient ingress/egress device 76, a lift device 78, a bed length extension device 80, a bed width extension device 82, a deck adjustment device 84, and a low air loss device 92. The operational devices 70-92 may also comprise powered devices for comfort, such as a temperature device 86, an entertainment device 88, and a lighting device 90. Other devices are also contemplated. For instance, operational devices comprising percussion devices, compression devices, vibration devices, and other patient therapy devices may also be employed.

The patient support system 28 comprises a control system 100 to control the operational devices 70-92 of the patient support apparatus 30, and a controller 102. The control system 100 controls the operational devices 70-92, or components thereof, to operate their associated actuators, control their pumps, control their valves, or otherwise cause the operational devices 70-92 to perform one of more of the desired functions. The controller 102 may be a functional subsystem of the control system 100. In other embodiments, the controller 102 may be a discrete system separate from the control system 100. In other words, the control system 100 and the controller 102 may be structurally integrated or separate. In one embodiment, the controller 102 is on-board the patient support apparatus 30 (e.g., coupled to the base 34, the footboard 54, or the like), and in another embodiment, the controller 102 is remotely located from the patient support apparatus 30 and in communication with the operational devices 70-92 disposed on-board the patient support apparatus 30. The controller 102 may communicate with the operational devices 70-92 via wired or wireless connections.

The controller 102 may comprise one or more microprocessors for processing instructions or for processing an algorithm stored in non-transitory memory 131 to control the operational devices 70-92. The control system 100 and/or controller 102 may comprise one or more microcontrollers, subcontrollers, field programmable gate arrays, systems on a chip, discrete circuitry, and/or other suitable hardware, software, or firmware that is capable of carrying out the functions described herein. Power to the operational devices 70-92 and/or the controller 102 may be provided by a battery power supply 104 or an external power source 106. Any type and number of sensors S may be included and in communication with the control system 100 and/or controller 102 to facilitate controlling the operational functions of the patient support apparatus 30.

The operational devices 70-92 may have many possible configurations for performing the predetermined functions of the patient support apparatus 30. Exemplary embodiments of the operational devices 70-92 are described further below, including the patient raising device 70, the immersion device 72, the patient turning device 74, the patient ingress/egress device 76, the lift device 78, the bed length extension device 80, the bed width extension device 82, the deck adjustment device 84, the temperature device 86, the entertainment device 88, and the lighting device 90. Further specifics regarding the exemplary devices are described in commonly owned U.S. patent application Ser. No. 15/353,179, filed on Nov. 16, 2016, which is hereby incorporated by reference herein in its entirety. Numerous devices other than those specifically described are contemplated, including a gatch adjustment device, a cleaning device, a coordinated motion device, a transport device, a cardiopulmonary resuscitation (CPR) device, an information transmission device (to the patient's electronic medical record (EMR) or electronic health record (EHR)), a sit-to-stand assist device, a cough detection device, a sleep detection device, among others. Any of the described and/or contemplated devices may be integrated into the guidance tools of the present disclosure.

The patient raising device 70 is configured to perform the function of moving the patient from a slouched position towards a non-slouched position by moving the patient towards the head end of the patient support apparatus 30. The patient raising device 70 may comprise a patient raising bladder structure within the mattress 40. The patient raising bladder structure may comprise patient raising inflation bladders that are connected together longitudinally so that each of the patient raising inflation bladders spans across a majority of a width of the mattress 40 below the patient, and the patient raising inflation bladders span a majority of a length of the mattress 40 below the patient. A progressive inflation scheme with the patient raising bladder structure is used to raise the patient from the slouched position to the non-slouched position. In response to a control signal from the controller 102, the patient raising inflation bladders are inflated and deflated to create a wave-like force directed towards the head end of the patient support apparatus 30 to push the patient toward the head end. In one example, only one of the patient raising inflation bladders is fully inflated at a time to create the wave-like force needed to raise the patient. Once fully inflated, each patient raising inflation bladder begins to deflate and the next adjacent patient raising inflation bladder toward the head end begins to inflate.

The immersion device 72 is configured to equalize and distribute pressure over a greater area of the surface of the body over the mattress 40, allowing for immersion of the patient. The immersion device 72 may comprise a bladder structure within the mattress 40 comprising, for example, elongate bladders spanning a majority of the length of the mattress 40 below the patient. In response to a control signal from the controller 102, the elongate bladders are selectively inflated or deflated to control the immersion of the patient within the mattress 40; i.e., the extent in which the patient "sinks into" the mattress. The bladder structure may also be configured move the patient from an off-center position toward a longitudinal centerline of the mattress 40, such as when the patient has shifted too far to one side or the other of the mattress 40. In response to a control signal from the controller 102, the elongate bladders are selectively inflated to guide the patient toward the longitudinal centerline of the mattress 40 when desired. Movement of the patient toward the longitudinal centerline may not be immediate, but may occur gradually as the elongate bladders remain inflated.

The patient turning device 74 is configured to perform the function of turning the patient and/or providing rotational therapy to the patient. The patient turning device 74 may utilize the patient centering/turning bladder structure as the immersion device 72. In response to a control signal from the controller 102, the elongate bladders are independently inflated to raise one side or the other of the patient. If used for rotation therapy, then the elongate bladders are used for rotation therapy by sequentially inflating/deflating the elongate bladders to raise one side of the patient to a desired angle, lower the patient, and then raise the other side of the patient to the desired angle such that the patient experiences a side-to-side rotation that shifts pressures between the patient and the mattress 40.

The patient ingress/egress device 76 is configured to perform the function of easing ingress and/or egress of the patient to and/or from the patient support apparatus 30. The patient ingress/egress device 76 comprises a main air bladder positioned within the mattress 40. The main air bladder is sized to extend substantially the full width of the mattress 40 and a majority of the length of the mattress 40. In an exemplary embodiment, the main air bladder comprises a single air bladder that can be inflated and deflated, depending on the needs of the patient or the caregiver. The controller 102 transmits a control signal to fully inflate the main air bladder to ease ingress and egress of the patient. For instance, if the main air bladder is less than fully inflated, e.g., to soften the mattress 40 and provide additional comfort to the patient, it can be difficult for the patient to move across the mattress 40 for ingress or egress. Accordingly, by fully inflating, and stiffening the mattress 40, movement across the mattress 40 can be made easier for the patient.

The lift device 78 is configured to lift and lower the patient between the minimum and maximum heights of the patient support apparatus 30, and intermediate positions therebetween. Referring to FIG. 1, a pair of column lifts are illustrated to perform this function. In other embodiments, the lift device 78 comprises a pair of lift arms vertically extending between the base 34 and the intermediate frame 36. The lift device 78 may comprise electromagnetic, electric, pneumatic, or hydraulic actuators, or other types of linear actuators. In response to a control signal from the controller 102, the lift device 78 operates to raise or lower the patient support surface 42, 43 relative to the base 34.

The bed length extension device 80 is configured to perform the function of adjusting a length of the patient support apparatus 30 to accommodate patients of greater than average height. In an exemplary embodiment, the bed length extension device 80 comprises a pair of actuators to move a bed extension between an unextended position and extended positions with respect to the intermediate frame 36. In some embodiments, the bed extension is movable from zero to at least twelve inches from the unextended position to a fully-extended position. In other embodiments, the bed extension is able to move less or more than twelve inches and may be extendable to any position between the unextended and fully-extended position with the actuators. The bed extension may have two, three, four, or nearly an infinite number of extended positions in which to be adjusted by the actuators.

The bed width extension device 82 is configured to perform the function of adjusting a width of the patient support apparatus 30 to accommodate patients of greater than average width. The bed width extension device 82 may operate in the same manner as the bed length extension device 80. The bed width extension device 82 may comprise two sets of actuators to move four bed extensions between unextended and extended positions with respect to the intermediate frame 36. In some cases only one actuator or one set of actuators is employed. In some embodiments, each of the bed extensions is movable from zero to at least twelve inches from the unextended position to a fully-extended position. In other embodiments, each of the bed extensions is able to move less or more than twelve inches and may be extendable to any position between the unextended and the fully extended position with the actuators. Each of the bed extensions may have two, three, four, or nearly an infinite number of extended positions in which to be adjusted by the actuators.

The deck adjustment device 84 is configured to articulate one or more of the deck sections of the patient support apparatus 30. In an exemplary embodiment, the deck adjustment device 84 comprises one or more deck actuators to move one or more of the deck sections of the patient support apparatus 30 including but not limited to the fowler section, the seat section, the thigh section, and the foot section. The actuators may comprise electric linear actuators extending between the intermediate frame 36 and the particular deck section being adjusted. For example, in response to a control signal from the controller 102, actuation of the deck actuator raises and lowers the fowler section at various inclination angles relative to the intermediate frame 36. Exemplary suitable linear actuators are supplied by LINAK A/S located at Smedevenget 8, Guderup, DK-6430, Nordborg, Denmark. It is contemplated that any suitable deck adjustment system may be utilized in conjunction with the patient support apparatus 30, so long as the deck adjustment is configured to move one or more of the deck sections.

The temperature device 86 is configured to adjust the temperature of the patient, the temperature of patient support apparatus 30, and/or the temperature of the room in which the patient resides for purposes of patient comfort, therapy, or recovery.

An entertainment device 88 may be activated or adjusted for patient comfort or therapeutic purposes. The entertainment device 88 may be activated or adjusted to provide soothing entertainment or background noise to the patient. In some embodiments the entertainment device 88 comprises at least one piece of entertainment equipment (e.g., television, radio, etc.).

The lighting device 90 may comprise one or more light sources and a dimmer apparatus connected to the light sources to provide lighting that makes the patient more comfortable. In some embodiments one or more of the light sources may be adjusted to be on, off, dimmed or brightened to provide soothing lighting to the patient. In other embodiments, active cancelling of noise may also be employed to make the patient more comfortable.

The low air loss device 92 is configured to reduce or relieve pressure and control moisture caused by the body of the patient in contact with the mattress. The low air loss device 92 may comprise bladders (e.g., the elongate bladders of the immersion device 72) that span a majority of the length of the mattress 40 below the patient. Further, the low air loss device 92 comprises microscopic holes within the patient support surface 43 of the mattress 40 that allow air to escape from the elongate bladders. The amount of pressure within each of the elongate bladders may be selectively controlled. The escaped air provides pressure and moisture reduction.

The operational devices 70-92 of the patient support apparatus 30 are controlled by the control system 100 in response to the user providing an input to a user interface 110. Referring to FIGS. 1 and 2, the patient support system 28 comprises the user interface 110 in communication with the controller 102 and configured to receive inputs from the user. Based on the input from the user to the user interface 110, the controller 102 generates and transmits a control signal to control the operational devices 70-92. The user interface 110 may comprise devices capable of being actuated by or receiving inputs from a user, such as the caregiver or the patient. The user interface 110 may be configured to be actuated in a variety of different ways, including but not limited to, mechanical actuation (e.g., hand, foot, finger, etc.), hands-free actuation (e.g., voice, foot, etc.), and the like. Each user interface 110 may comprise a button, a gesture sensing device for monitoring motion of hands, feet, or other body parts of the caregiver (such as through a camera), a microphone for receiving voice activation commands, and a sensor (e.g., infrared sensor such as a light bar or light beam to sense a user's body part, ultrasonic sensor, etc.). In some embodiments, the user interface 110 comprises a voice recognition system 137 in communication with the controller 102. The voice recognition system 137 comprises a voice actuation interface 138 such as microphone in communication with the controller 102 to receive voice activation commands from the user. The voice activation commands may be associated with the operational functions of the patient support apparatus 30, such as to control the operational devices 70-92 in a manner to be described. It should be appreciated that any combination of user interfaces 110 may also be utilized for any of the operational devices 70-92.

The user interface 110 may be located on one of the side rails 44, 46, 48, 50, the headboard 52, the footboard 54, or other suitable locations. FIG. 1 shows the user interface 110 is located on two of the side rails 46, 48 and the footboard 54. FIG. 1 further shows the user interface 110 located on the footboard 54 and rotatably mounted to the same. Additionally or alternatively, the user interface 110 may also be located on a mobile device 156 (e.g., iWatch®, iPhone®, iPad®, or similar electronic devices). FIG. 1 shows a caregiver holding the mobile device 156 comprising a touchscreen display 114 with the user interface 110. The touchscreen display 114, as described throughout the present disclosure, is configured to provide instructions, information and other output (e.g., graphics) to the user, and further configured to receive input from the user, such as through manual actuation, as described above.

The mobile device 156 is configured to receive the inputs from the user in any suitable manner including, but not limited to, mechanical actuation, voice commands, and gesturing. The user typically provides the input to the mobile device 156 through the touch of a virtual button displayed on the touchscreen display 114. In response to the inputs from the user, the user interface 110 mobile device 156 may generate input signals. In one embodiment, the controller 102 receives the input signals from the user interface 110 based on the inputs from the user to the mobile device 156.

The patient support system 28 further comprises an information output device 112 in communication with the controller 102 and configured to provide instructions to the user, such as the caregiver or the patient. In one embodiment, the information output device 112 comprises a display displaying the instructions and other information to the user. In another embodiment, the information output device 112 comprises speakers providing audible instructions to the user. Combinations of the display and speakers are present in many embodiments. In a further embodiment, the user interface 110 and the information output device 112 are embodied on the touchscreen display 114. Capacitive touchscreens and other types of displays capable of receiving a touch-sensitive input may be employed.

Figure 3:
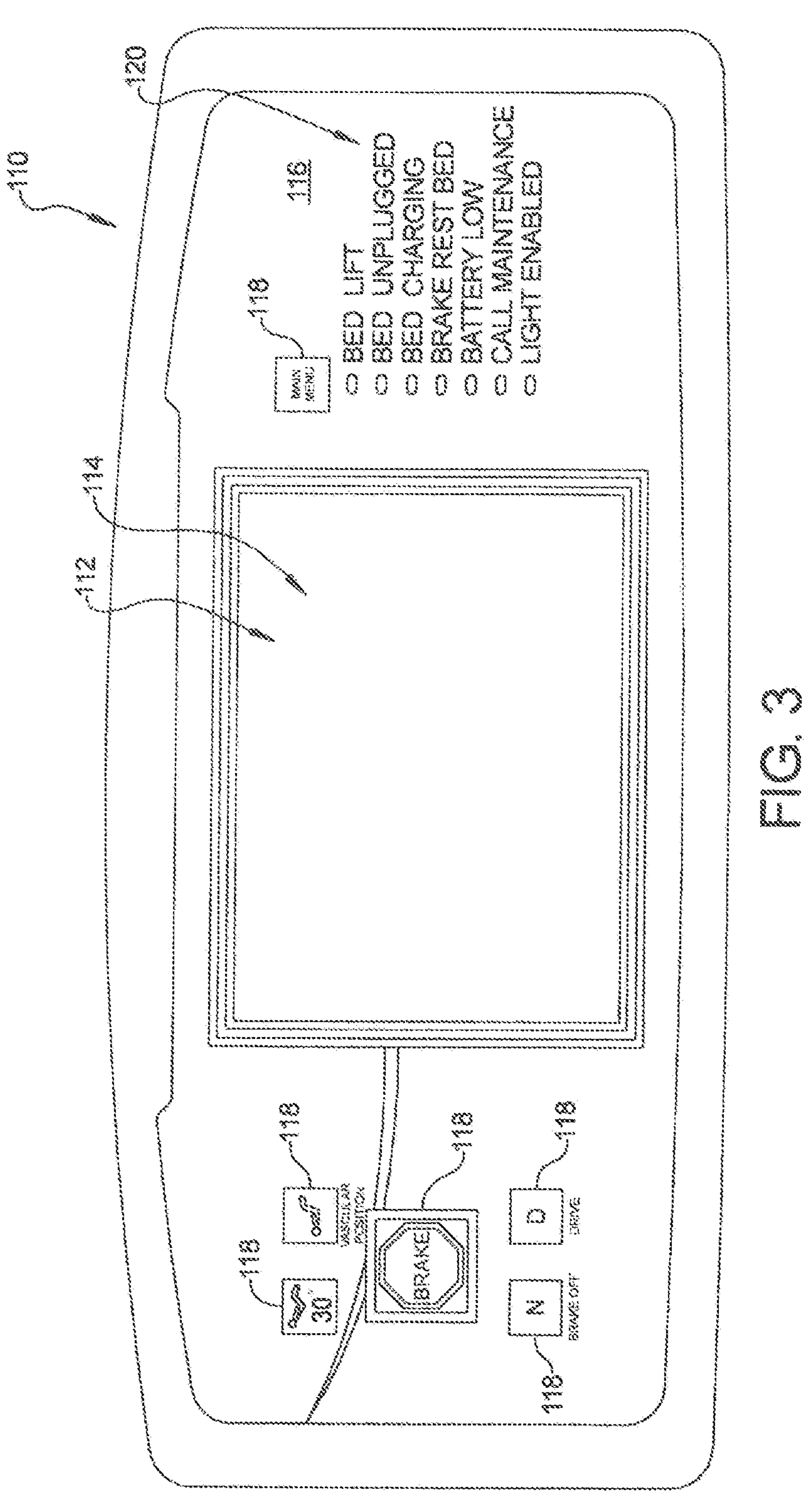
FIG. 3 a perspective view of a user interface and an information output device.

Referring to FIG. 3, an exemplary user interface is shown. The user interface 110 may comprise a front cover 116. One or more virtual and/or tactile buttons 118 may be disposed on the front cover 116 in any suitable configuration. The buttons 118 integrated into the front cover 116 may be indicative of operational functions of the patient support apparatus 30, particularly those more frequently used by caregivers. FIG. 3 shows tactile buttons associated with an emergency brake feature, a "drive" feature, and a "brake off" feature, among others. Status indicators 120 may be disposed on the front cover 116 in any suitable configuration. FIG. 3 illustrates several status indicators in columnar form with each status indicator 120 comprising a light (e.g., light emitting diode) corresponding to a particular status (e.g., bed unplugged, bed charging, etc.). The status indicators 120 provide users with warnings and other relevant information. FIG. 3 further shows the information output device 112 within the front cover 116 and positioned intermediate the buttons 118 and the status indicators 120. The information output device 112 of FIG. 3 includes the touchscreen display 114 previously described that also comprises a portion of the user interface 110.

Figure 4:
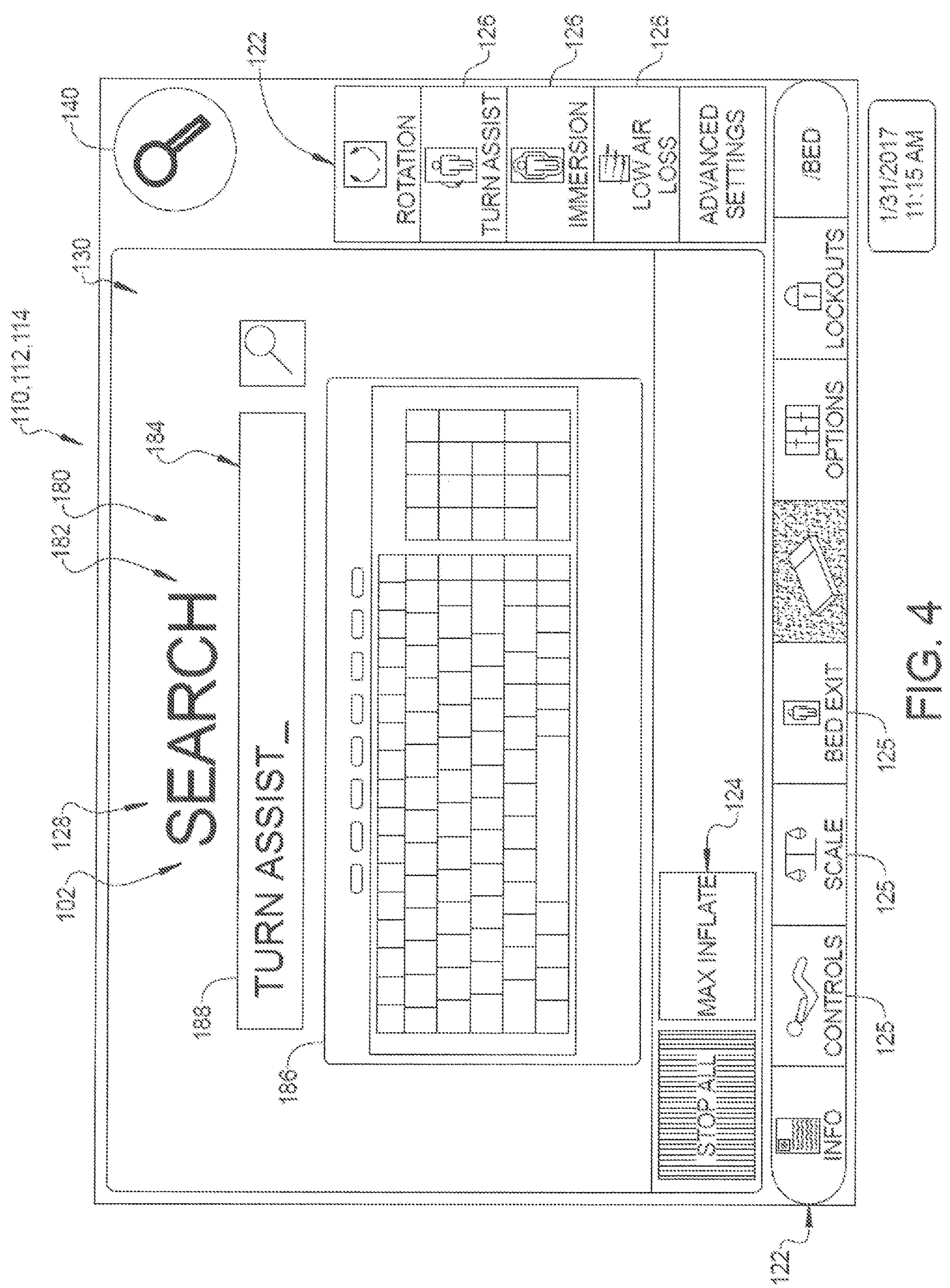
FIG. 4 is a touchscreen display providing functionality for the user to input a search query. A virtual keyboard is displayed and actuatable by the user to input the search query.

The controller 102 may be configured to execute a software application. The software application is configured to display user menus 130 navigable by the user to control the operational functions of the patient support apparatus 30, such as to control the operational devices 70-92. In general, the user menus 130 may comprise any suitable output displayed with the information output device 112 to facilitate efficient operation of the patient support system 28. Any suitable format of the user menus 130 is contemplated, including but not limited to lists, grids and/or arrays of text, graphics and/or icons comprising indicia 124. The indicia 124, as used herein, may comprise text, graphics, and the like, selectable by the user with the user interface 110. In the exemplary embodiments illustrated in FIGS. 4-6, the indicia 124 is within a working area 128 of the user menu 130. Indicia 125 representative of predetermined one or more of submenus and/or indicia 126 representative of one of more operational functions of the patient support apparatus 30 may be provided and arranged on one or more taskbars 122. FIG. 4 shows a horizontal one of the taskbars 122 comprising the indicia 125 and a vertical one of the taskbars 122 comprising the indicia 126. The taskbars 122 may remain generally static, whereas the working area 128 is provided to display generally dynamic text, graphics, and other media associated with any particular one of the user menus 130. Through actuation of the user interface 110 (e.g., touching virtual buttons of the touchscreen display 114), the user may navigate through the user menus 130 of the software application of the patient support system 28.

Controlling the operational functions of the patient support apparatus 30 may require performing several steps with the software application. In one example, the user may be required to provide multiple inputs to the user interface 110 to navigate the user menus 130 to control the desired one or more of the operational functions of the patient support apparatus 30. The ability of the user to do so may depend on the familiarity of the user with the software application, the touchscreen display 114, technology generally, and other factors. Often, the operational devices 70-92 to be controlled by the user may not be represented on the user menu 130 currently being displayed with information output device 112. The user may be required to perform one or more user-performed actions (e.g., providing input(s) to the user interface 110) in order to navigate the user menus 130 of the software application, after which the user is provided with the option to control the desired one or more of the operational devices 70-92. Those unfamiliar with navigating the software application may experience appreciable difficulty with doing so. In other instances, the user may simply lack the technological savvy to navigate the user menus 130 of the software application. It is therefore one of many advantages of the subject disclosure to provide improved guidance tools that are accessible through the user interface 110 and/or information output device 112.

According to an exemplary embodiment of the present disclosure, the controller 102 is configured to receive input signals from the user interface 110 based on the inputs from the user to the user interface 110. In certain embodiments, the inputs from the user to the user interface 110 comprise the user touching the touchscreen display 114. For any number of reasons, the user may provide a search request to the user interface 110 in order to locate the user menu 130 with the option to control the desired one or more of the operational devices 70-92. For example, the user may have unsuccessfully attempted to navigate the user menus 130 of the software application to the menu configured to control the desired one or more of the operational devices 70-92. In another example, the user may anticipate difficulty with navigating the user menus 130 and/or prefers to save time by seeking assistance. In certain embodiments, the search request comprises a search button 140 on the user interface 110, and more particularly the touchscreen display 114. FIG. 4 shows the search button 140 positioned in an upper-right corner of the touchscreen display 114.

Subsequent to the user actuating the search button 140, the information output device 112 outputs a prompt requesting further information. Referring to FIG. 4, a search screen 178 is provided. The user interface 110 is configured to receive inputs from the user comprising a search query 184 on a search menu 182. The search menu 182 may be part of one of the user menus 130. The search menu 182 may be displayed with the information output device 112 consequent to the user actuating the search button 140. The user may navigate the software application to the search menu 182 through other submenus as well.

Figure 5:
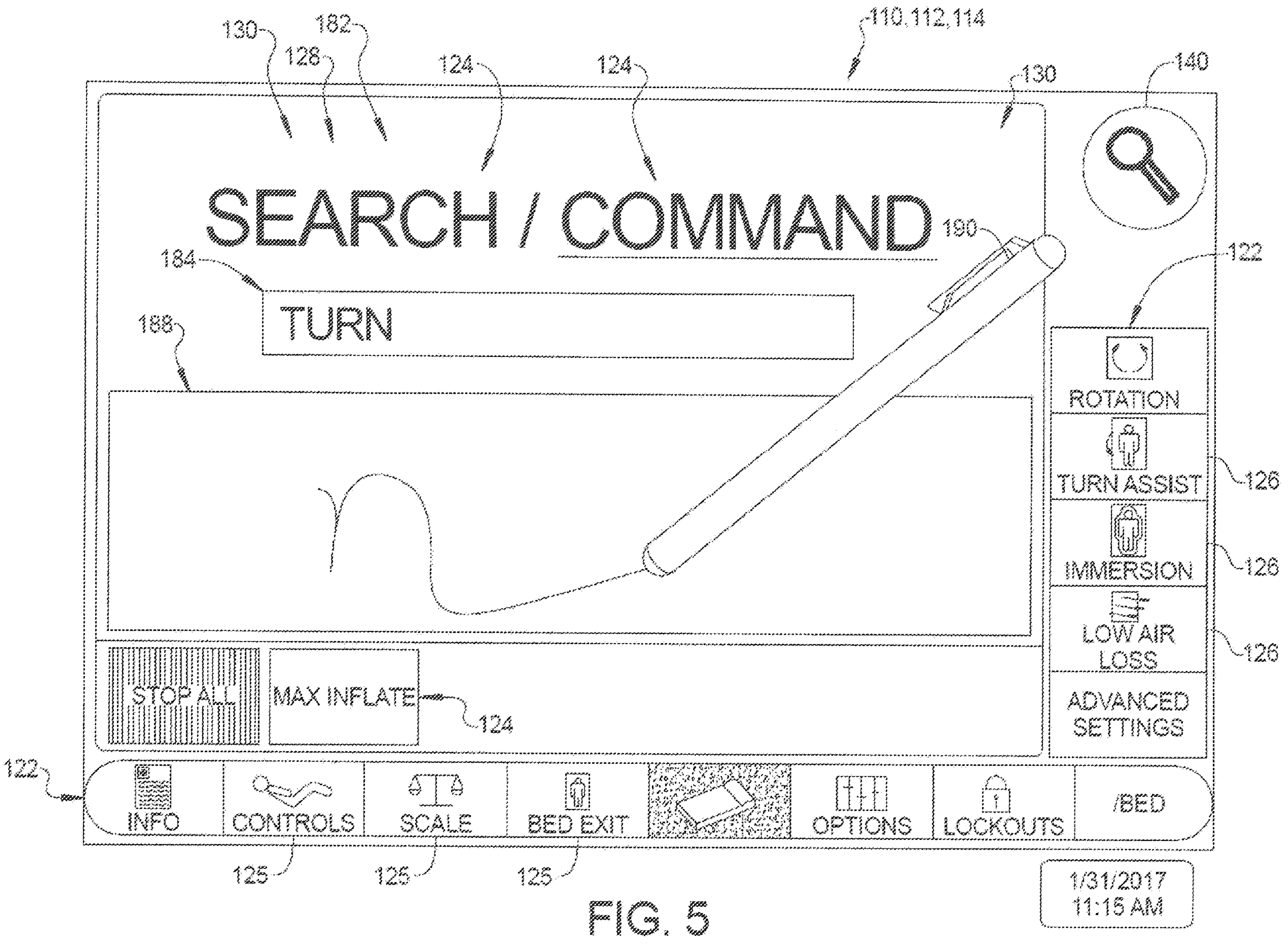
FIG. 5 is the touchscreen display of FIG. 4 providing alternative functionality for the user to input the search query. A field is displayed and configured to receive input from the user via a stylus, touching, or other input device.

FIG. 4 shows the search menu 182 with virtual keyboard 186 provided with the information output device 112. The virtual keyboard 186 comprises alphanumeric keys selectable by the user through touching the keys on the touchscreen display 114. The letters or numbers corresponding to the selected alphanumeric keys is displayed and entered as the search query 184. FIG. 5 shows the search menu 182 with a field 188 configured to receive input from a stylus 190 controlled by the user in a manner to be described. In such an embodiment, the user may operate the stylus to virtually write within the field 188. The letters or numbers corresponding to the virtual writing is displayed and entered as the search query 184. Alternatively, the touchscreen display 114 may be configured to permit the user to virtually write with one's finger as opposed to the stylus 190. Other suitable ways of inputting the search query 184 into the field 188 may be employed.

The search query 184 may comprise the search request received by the controller 102 to determine the search results. For example, the search query 184 comprises a query received by a search engine to provide search results on the touchscreen display 114. The search results may be selectable on the touchscreen 114 to comprise the search request. As mentioned, the search query 184 may be provided as entering the letters or numbers on the virtual keyboard 186, or operating the finger or stylus to virtually write within the field 188.

In certain embodiments, the information output device 112 is configured to provide search results and instructions to the user with the search results related to operational functions of the patient support apparatus 30. The controller 102 is configured to determine the search results in response to the search query 184. The search results are provided to the user with the information output device 112. The user may select one of the search results with the user interface 110. Consequently, the controller 102 receives the user selection from the search results with the user interface 110, such as the touchscreen display 114. Based on the user selection, the controller 102 is configured to determine the user menu 130 and transmits an output signal to provide the user menu 130 to the user with the information output device 112. The user menu 130 may include one or more features associated with the selected operational function of the patient support apparatus 30 from the search query 184. From the features included in the user menu 130, the user may provide a further input to the user interface 110 to cause the feature(s) from the selected operational function to be performed. The above example may be considered an indirect control protocol to control the operational functions 70-92 of the patient support apparatus 30. In other words, the search query 184 provided to the user interface 110 produces search results and/or the user menu 130 to receive the further input to ultimately result in the operational function to be performed. Another direct control protocol to be described may be considered to control the operational functions 70-92 without requiring the intermediate further input.

An exemplary operation of the indirect control protocol is described with reference to FIG. 4. In the present example, the user interface 110 and the information output device 112 are embodied by the touchscreen display 114. The user actuates the search button 140 displayed on the touchscreen display 114. In response, the information output device 112 may output to the user the search screen 178. The user may provide the search parameters to the search query 184, such as by entering the letters or numbers on the virtual keyboard 186 or operating the finger or stylus to virtually write within the field 188. In one example, the user provides the requested information and inputs to the touchscreen display 114—"turn assist." The controller 102 determines the search results based on the input signals, such as by matching the received input to a database associating keywords with the appropriate one or more operational devices 70-92. In this example, based on the use of the words "turn" and "assist," the controller 102 determines the search results comprise the user-performed actions to be performed by the user in order to operate the patient turning device 74. In some embodiments, the information output device 112 may provide the user with a confirmatory request. The confirmatory request may simply repeat the provisionally selected one of the operational functions of the operational devices 70-92 (e.g., "Turn Assist" of the patient turning device 74), and/or provide additional information about the same. For example, the information output device 112 may provide, visually and/or audibly, "Are you trying to operate the Patient Turning Device? Would you like assistance'?" The user may provide input agreeing to further assistance if desired.

Less precise inputs by the user may require more elaborate determinations by the controller 102 as to the intentions of the user. For example, the user may input via the virtual keyboard 186 to the field 188, "bed sores," or "changing the sheets." Utilizing artificial intelligence (AI), algorithms, a database of keyword associations, and the like, the controller 102 is configured to determine the most relevant search results to present to the user. In certain embodiments, the information output device 112 may be configured to provide a list of search results for the user to further consider and from which to select. For example, in response to the user inquiring about bed sores, the touchscreen display 114 may provide a pop-up window providing indicia 124 representative of the patient turning device 74, as well as the immersion device 72 and the low air loss device 92, each of which may be desirable to alleviate the pressure that causes bed sores. Options may be provided in every instance or in some instances when the controller 102 is unable to determine the search results for a particular operation with a confidence index above a confidence threshold. The provided options may be ranked based on perceived relevance.

Whether from the search query 184 itself, the confirmatory request, or a selected one of the list of options, the user menu 130 associated with the patient turning device 74 is provided on the touchscreen display 114. The user menu 130 may include an arrangement of the feature(s) associated with the patient turning device 74, for example, turn left, turn right, turn side to side, a patient turning program, a timer for the program, and the like. The user may then provide the further input to the touchscreen display 114 to select one or more of the features. An input signal is sent to the controller 102, which controls the patient turning device 74 in the manner desired by the user.

As mentioned, the patient support system 28 provides for the direct control protocol in which the operational functions 70-92 without requiring the intermediate further input. The direct control protocol will be described as a variant of the above example for controlling the patient turning device 74. The user actuates the search button 140 displayed on the touchscreen display 114. In response, the information output device 112 may output to the user the search screen 178. The user may provide the search parameters to the search query 184, such as by entering the letters or numbers on the virtual keyboard 186 or operating the finger or stylus to virtually write within the field 188. For example, the user provides the input to the touchscreen display 114—"side to side turn assist every five minutes." The controller 102 determines the search results based on the input signals, such as by matching the received input to a database associating keywords with the appropriate one or more operational devices 70-92. In this example, based on the use of the words "turn" and "assist," the controller 102 determines the desired actions including operating the patient turning device 74. Further, based on the use of words "side to side" and "every five minutes," and in particular in combination with the words "turn" and "assist," the controller 102 determines the desired actions include turning a patient turning program in which the patient is repeatedly turned to the left for five minutes, then turned to the right for five minutes. Without providing search results, the confirmatory request, and/or the list of options, the controller 102 automatically controls the patient turning device 74 based on the determination of the desired actions. The direct control protocol may provide a more streamlined user experience, and may be particularly useful with moderate to experienced users with previous knowledge of the keywords (i.e., the search query 184) required to effectuate certain actions of the operational devices 70-92.

It is to be understood that the exemplary operations described above are non-exhaustive. A user may receive guidance for any operational feature of the patient support apparatus 30 controllable from the user interface 110. For example, the guidance tools facilitate control of the immersion device 72 or the low air loss device 94. For another example, the guidance tools facilitate ordering replacement parts for the patient support apparatus 30 with the user interface 110.

In certain embodiments, the information output device 112 comprising the touchscreen display 114 may provide the user with a list of frequently asked questions (FAQs). In such an embodiment, the user may select, via the touchscreen display 114, one of the FAQs that the user perceives to be most related to subject matter of the search request. Providing the list of FAQs may provide additional or alternative means for the user to provide the search request to the user interface 110. Other manners by which the search request may be provided are described throughout the present disclosure. In one example, the search request may be provided verbally to the voice recognition system 137 with the voice actuation interface 138.

In some embodiments, the touchscreen display 114 comprising the user interface 110 and the information output device 112 displays the field 188 configured to receive shorthand commands 192 corresponding to operational functions of said patient support apparatus 30. The shorthand commands may be written shortcuts configured to enable, disable, and/or perform operational functions of the patient support apparatus 30. The shorthand commands 192 may be provided to the field 188 with freeform virtual writing, such as with a finger, stylus 190, or other suitable object or device, and/or to the search query 184 (e.g., by entering the letters or numbers on the virtual keyboard 186).

The controller 102 is in communication with the touchscreen display 114. The controller 102 receives input signals from the touchscreen display 114 based on one of the shorthand commands 192 from the user provided to the touchscreen display 114. The controller 102 is configured to determine one of the operational functions of the patient support apparatus corresponding to the one of shorthand commands. In certain embodiments, the shorthand commands may be predefined in a referential database stored on the non-transitory memory 131. Exemplary shorthand commands and their predefined and corresponding operational function are provided in Table 1. For example, if the user virtually writes "SC" within the field 188 with the stylus 190, the controller 102 determines that a weight scale application is to be displayed on the touchscreen display 114. Another example comprises the user virtually writing "LU" within the field 188 with the stylus 190, after which the information output device 112 may provide the user with a "Lift Up" submenu 152 on the touchscreen display 114.

TABLE 1

Exemplary Shortcuts for User Input to the Field

| Function | Shorthand commands |
|---|---|
| Lift Up/Down | LU, LD |
| Fowler Up/Down | FU, FD |
| Gatch Up/Down | GU, GD |
| Scale | SC |
| Enable Bed Exit/Disable | BEE, BED |
| Brake Enable/Disable | BE, BD |
| Patient Lockout Enable/Disable | PLE, PLD |
| Bed Monitoring Enable/Disable | BME, BMD |
| Home Menu | H |
| Stop | S |
| Fowler 30 Degrees | F30 |
| About Menu | A |
| Electronic Medical Record (EMR) | EMR |
| Battery Status | BS |
| Diagnostics | D |

After the shorthand commands 192 are virtually written within the field 188, the controller 102 is configured to control the one of operational functions of the patient support apparatus 30, perhaps automatically; i.e., direct control protocol. Additionally or alternatively, the shorthand commands 192 are virtually written within the field 188, the controller 102 is configured to provide search results of relevant operational functions of the patient support apparatus 30; i.e., indirect control protocol. An additional input to the touchscreen display 114 (e.g., a tap with the stylus 190 or actuating a "Submit" button) may be required before the corresponding action is taken. The present disclosure further contemplates the submenus may also include shorthand commands specific to a particular one of the submenus (e.g., "Z" to zero the virtual scales in the weight scale application; "LW" for units of pounds in the weight scale application, etc.). It is further contemplated that the shorthand commands 192 may be provided verbally to the voice recognition system 137 with the voice actuation interface 138.

As mentioned, the patient support system 28 may comprise the voice recognition system 137 with the voice actuation interface 138 adapted to receive voice activation commands from the user, such as to control operational functions of the patient support apparatus 30. A voice activation enabling device 139 communicates with the controller 102. The voice activation enabling device 141 may be mounted to the base 34, the intermediate frame 36, the side rails 44, 46, 48, 50, the headboard 52, the footboard 54, or other suitable locations on the patient support apparatus 30. The voice activation enabling device 141 may also be located on the mobile device 156 or otherwise remote from the patient support apparatus 30. The voice activation enabling device 141 is actuated by the user to enable voice activation commands. In some embodiments, if the voice activation enabling device 141 is not actuated before voice activation commands are made, the controller 102 will not respond to the voice activation commands. In other embodiments, the voice activation interface 138 is always enabled and triggered by an initializing voice command, such that the voice activation interface 138 is ready to receive voice activation commands once the initializing voice command is given. Based on the vocal input from the user provided to the voice recognition system 137, the voice recognition system 137 provides input signals to the controller 102 for functions to be disclosed. Exemplary voice recognition systems may include Dragon NaturallySpeaking™ Medical from Nuance Communications, Inc. (Burlington, Mass.), Siri™ by Apple (Cupertino, Calif.), and Alexa™ by Amazon, Inc. (Seattle, Wash.).

The voice recognition system 137 may be a computer program that works as an intelligent personal assistant and knowledge navigator similar to Siri™ or Alexa™. In embodiments utilizing the voice recognition system 137, the patient support system 28 comprises the patient support apparatus 30, the user interface 110, the voice actuation interface 138 configured to receive voice actuation commands from a user, and an information output device 112 configured to provide audible and/or visual instructions to the user. The controller 102 is in communication with the user interface 110 and the information output device 112. The controller 102 is configured to receive input signals from the user interface 110 based on the voice commands from the user to the voice actuation interface 138. The controller 102 is further configured to determine the search results for the user based on the input signals received from the voice recognition system 137. Consequently, many of the operational functions of the patient support apparatus 30 may be controlled solely through verbal exchanges with the voice recognition system 137 and information output device 112. It is to be appreciated that the voice recognition system 137 may be used with either indirect control protocol or the direct control protocol.

An exemplary operation of the guidance tools using the voice recognition system 137 is described in which the user interface 110 comprises the voice actuation interface 138 and the information output device 112 comprises the speakers. In such a configuration, the user may provide the search parameters through speaking, and receive the search results audibly and/or visually. The user actuates the search button 140 displayed on the touchscreen display 114, and the information output device 112 may output to the user a search screen 178, as shown in FIG. 4. In certain embodiments, the information output device 112 comprises the speakers that may output a phrase, for example, "Please say 'How do I' and state your question," or "Please say how I can be of assistance." Additionally or alternatively, the information output device 112 comprising the touchscreen display 114 may display the output visually to invite the user to vocally provide specifics of the search request to the voice actuation interface 138.

The user provides the further information comprising the search request with the user interface 110. In one example, the user provides the requested information and verbally inputs to the voice actuation interface 138, "How do I turn on 'Turn Assist?'" The voice recognition system 137 receives the input and transmits the input signals to the controller. The controller 102 determines the search results based on the input signals, such as by matching the received voice input to a database associating keywords with the appropriate one or more operational devices 70-92. In this example, based on the user speaking the words "turn" and "assist," the controller 102 determines relevant search results, including operating the patient turning device 74. Other, perhaps less precise, voice inputs to the voice actuation interface 138 may require more elaborate determinations by the controller 102 as to the intentions of the user. For example, the user may say to the voice actuation interface 138, "He has bed sores," or "I need help changing the sheets." Utilizing artificial intelligence (AI), algorithms, a database of keyword associations, and the like, the controller 102 is configured to determine the most relevant search results to present to the user. In certain embodiments, the information output device 112 may be configured to provide options for the user to further consider and from which to select. For example, in response to the user inquiring about bed sores, the touchscreen display 114 may provide a pop-up window providing indicia 124 representative of the patient turning device 74, as well as the immersion device 72 and the low air loss device 92, each of which may be desirable to alleviate the pressure that causes bed sores. Options may be provided in every instance or in some instances when the controller 102 is unable to determine the search results for a particular operation with a confidence index above a confidence threshold. The confidence index may be provided to the user such that the user receives feedback as to how the system perceived the search request. Subsequently, the user selects one of the options with the selection comprising the search request that is provided as an input signal to the controller 102.

Figure 6:
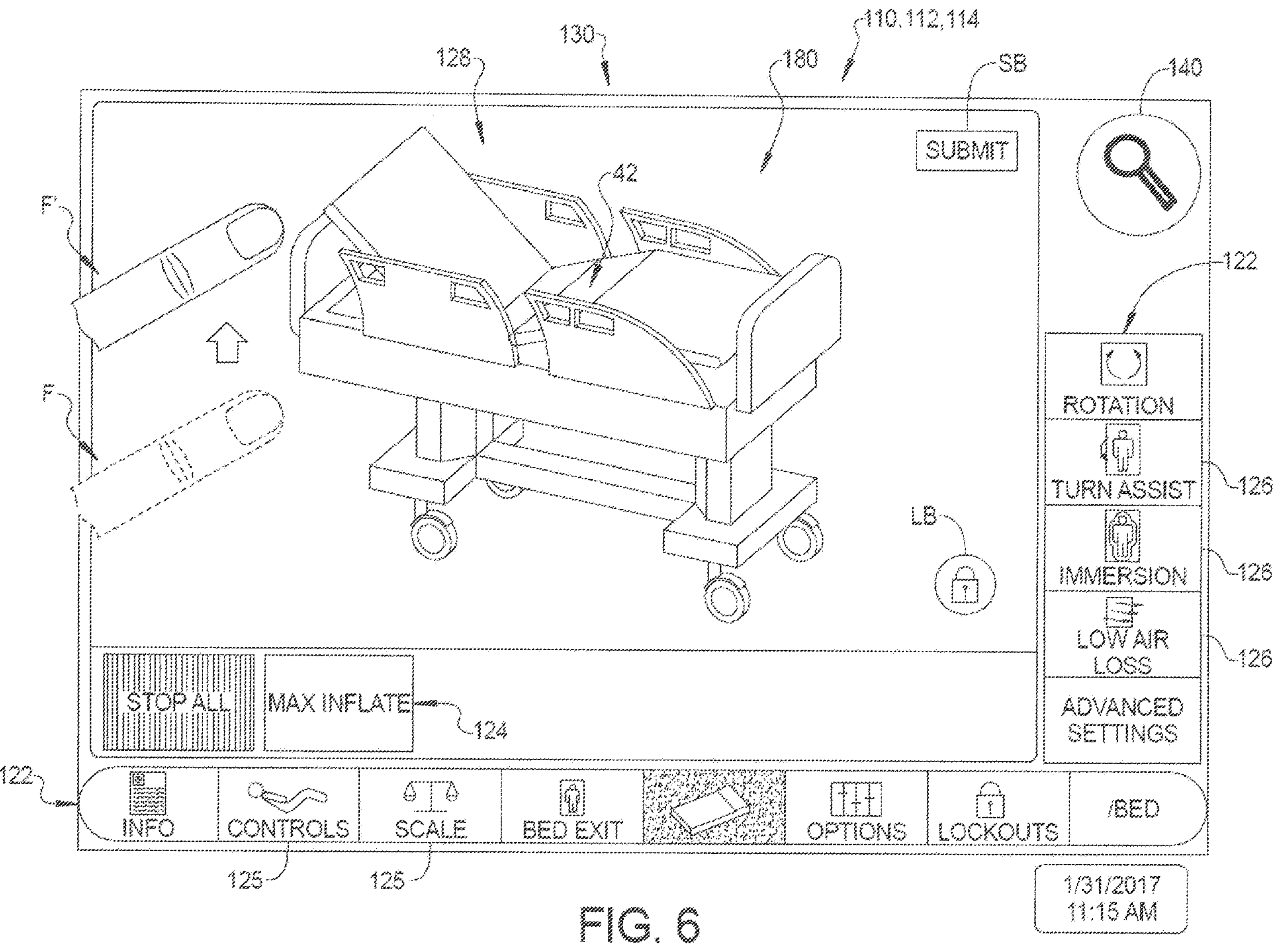
FIG. 6 is the touchscreen display of FIG. 4 displaying a pictorial representation of the patient support apparatus. The user may engage the pictorial representation to control operational functions of the patient support apparatus.

The user menus 130 displayed on the touchscreen display 114 are designed to provide a well-organized, aesthetically appealing user experience. The patient support system 28 of the present disclosure further contemplates additional ways of controlling the operational features of the patient support apparatus 30 in a particularly intuitive manner. Referring now to FIG. 6 at least a portion of the indicia 124 selectable by the user comprises a pictorial representation 180 of the patient support apparatus 30. Stated differently, at least a portion of the pictorial representation 180 comprises indicia 124 selectable by the user to control the operational functions of the patient support apparatus 30. In such an embodiment, the touchscreen display 114 embodies the user interface 110 with the user engaging the pictorial representation 180 of the patient support apparatus 30 on the touchscreen display 114. The pictorial representation 180 may be a static or dynamic two-dimensional graphical object, as shown, or three-dimensional graphical object. The pictorial representation 180 may be realistic (e.g., a computer aided design (CAD) model) or simplified or stylized to any extent. FIG. 6 shows the pictorial representation 180 within the working area 128 of the touchscreen display 114 with the taskbars 122 bounding the working area 128 on the bottom and right sides. In other words, the pictorial representation 180 occupies only a portion of the touchscreen display 114, however it is contemplated that the pictorial representation 180 may occupy an entirety of the touchscreen display 114 without the taskbars 122 and other indicia, menu buttons, and the like. In such a variant, the indicia, menus, and the like may "pop up" while directly engaging the pictorial representation 180 of the patient support apparatus 30.

The pictorial representation 180 may be rotated and/or repositioned (e.g., panned) through inputs to the touchscreen display 114 in manners to be described. Similarly, the user may zoom in or zoom out on the pictorial representation 180 through input to the touchscreen display 114, such as, for example, by a pinching motion with two of the user's fingers touching the touchscreen display 114. The controller 102 may transmit an output signal to the touchscreen display 114 to provide an updated display of the pictorial representation 180 being rotated, panned, or zoomed in a manner corresponding to the input. FIG. 6 shows a user menu 130 comprising a perspective view of the pictorial representation 180. In other embodiments, CAD software may be provided to permit the user to manipulate the pictorial representation 180 in the manner desired. Multiple views (e.g., plan view, perspective view, etc.) of the pictorial representation 180 may be displayed on the touchscreen display 114. Image and/or video-based tutorials for effectively engaging the pictorial representation 180 may be provided with the information output device 112.

The inputs from the user to the touchscreen display 114 may comprise directly engaging the pictorial representation 180 to control one or more operational functions of the patient support apparatus 30. Controlling the operational functions may include controlling the operational devices 70-92 of the patient support apparatus 30, or any other operational function. Engaging the pictorial representation 180 may include touching the touchscreen display 114 with a finger, hand, stylus, or any other suitable object or device. In particular, the user may touch a desired component or feature of the pictorial representation 180 of the patient support apparatus 30 displayed on the touchscreen display 114 to produce a corresponding result of the patient support apparatus 30. The corresponding result may be effectuated without need of further input to the touchscreen display 114. For example, FIG. 6 shows a perspective view of the patient support apparatus 30. The user touches the touchscreen display 114 with a finger F (shown in phantom), and slides the finger F upwardly as shown. In such an example, the user engagement is a continuous motion while directly engaging the pictorial representation 180 on the touchscreen display 114. In particular, the user touches the relevant portion of the pictorial representation 180 on the touchscreen display 114. The pictorial representation 180 may move in a manner corresponding to the input provided by the user with the touchscreen display 114. Either before or after the corresponding result of the patient support apparatus 30 is effectuated, the controller 102 may transmit an output signal to the touchscreen display 114 to provide an updated display of the pictorial representation 180. The above example may be considered to control operation of the patient raising device 70 by directly engaging the pictorial representation 180 of the patient support apparatus 30. Another exemplary operational function 70-92 controllable by direct engagement of the pictorial representation 180 of the patient support apparatus 30 includes moving the fowler section to increase or decrease the fowler deck angle.

In certain embodiments, the user may manipulate the pictorial representation 180 on the touchscreen 114 before or after engaging the desired portion of the pictorial representation 180. Certain operational devices 70-92 of the patient support apparatus 30 that are controllable via the touchscreen 114 may not be visible upon display of the pictorial representation 180. For example, the indicia 124 that are icons representative of the operational devices 70-92 of the patient support apparatus 30 may be too small to be effectively selected via the touchscreen 114, or the indicia 124 may be positioned on a side opposite what is displayed initially. The user may rotate, pan, and/or zoom in on or out of the pictorial representation 180 to more effectively visualize the indicia 124 representative of the operational devices 70-92 to be controlled. Further, as the user provides the input to zoom in and zoom out, the pictorial representation 180 may be refreshed or be re-rendered to provide more or less detail. For example, the pictorial representation 180 shown in FIG. 6 shows relatively little detail of the patient support apparatus 30. Should the user provide an input to the touchscreen 114 to zoom in on the side rail, the pictorial representation 180 of the headboard may be rendered to show structures, devices, and/or features not previously shown. Conversely, should the user provide an input to the touchscreen 114 to zoom out, the features previously shown may be removed or genericized as the pictorial representation 180 shows a greater portion of the patient support apparatus 30. In other embodiments, CAD software may be provided to permit the user to manipulate the pictorial representation 180 in the manner desired.

As mentioned, the user may touch a desired component or feature of the pictorial representation 180 of the patient support apparatus 30 displayed on the touchscreen display 114. In certain embodiments, the desired component or feature is visually emphasized such that the user is aware with which component or feature the user is interacting. The visual emphasis may include such as a change in color, a ring or halo, a marking (e.g., an arrow, as asterisk, etc.), or an image. The visual emphasis may also include altering the size, shape, look, and/or feel of the desired component. The visual emphasis may be temporary for a fixed period of time, or the desired component or feature may remain visually emphasized until the pictorial representation 180 is manipulated as desired. Rotation, panning, and zooming in or out of the pictorial representation 180 through input to the touchscreen display 114, as described, may assist with ensuring the desired component or feature is easily selectable. The user may engage the indicia 116 through, for example, engaging the touchscreen display 114 or double clicking with the CAD software to select the corresponding portion of the patient support apparatus 30. Should the user provide an input that may, as determined by the controller 102, be applicable to more than one feature or component of the patient support apparatus 30 shown in the pictorial representation 180, a prompt may be provided to confirm which component should be engaged. Such a confirmation may be particularly useful when several components are illustrated within a small area. In other embodiments, the confirmatory prompt may be provided in every instance, including those when the input from the user is clearly directed to a particular component, and/or instances where uncertainty is low as which feature or component is being selected.

The resulting position of the pictorial representation 180 may be interpreted by the controller 102 as the desired position of the patient support surface 42 or other suitable component of the patient support apparatus 30. The touchscreen display 114 provides an input signal to the controller 102 as previously described. The controller 102 provides a corresponding signal to control the operational devices 70-92 of the patient support apparatus 30, in this example the lift device 78. Consequently, the patient support surface 42 or other suitable component moves in a manner corresponding to the user input to the touchscreen display 114. Unlike some conventional user interfaces that use buttons such as "up" and "down" or "+" and "—", embodiments of the present disclosure correlates the movement of the user's finger F relative to the pictorial representation 180 of the patient support apparatus 30, to command movement providing for a more intuitive operation of the patient support apparatus 30.

Furthermore, the user may engage the pictorial representation 180 in a manner that provides simulated movements of the pictorial representation 180 on the touchscreen display 114. The simulated movements of the pictorial representation 180 may or may not provide corresponding movements of the patient support apparatus 30. In one non-limiting example, a lever (not shown) associated with the patient support apparatus 30 may be represented in the pictorial representation 180. Actuation of the lever (on the patient support apparatus 30) is adapted to provide a corresponding movement of a physical structure of the patient support apparatus 30. The user may engage the pictorial representation 180 on the touchscreen display 114 to simulate the movement of the representation of the lever and view the corresponding result virtually on the touchscreen display 114. In certain embodiments, the user, perhaps knowing the result from the simulation provided on the touchscreen display 114, may subsequently elect to engage the pictorial representation 180 in a manner that provides corresponding movements of the patient support apparatus 30.

In certain embodiments, the user may engage the pictorial representation 180 displayed on the touchscreen 114 to move the pictorial representation 180 without initially effectuating the corresponding operation of the patient support apparatus 30. A "Submit" button SB is provided in the working area 128 of the user menu 130. Once the user is satisfied with, for example, the updated position of the pictorial representation 180, the user actuates the button SB to facilitate the corresponding movement of the patient support apparatus 30. In another embodiment, the user may be required to "double click" in order to initiate controlling the corresponding operation function of the patient support apparatus 30. In still another embodiment, a "pop-up window" may be generated requesting confirmation of intended operational function to be controlled. In still yet another embodiment, the corresponding operation of the patient support apparatus 30 occurs after the user stops engaging the pictorial representation 180 displayed on the touchscreen 114. Voice confirmation may alternatively or additionally be utilized. Using a button, a pop-up window, voice confirmation, and/or similar confirmatory measures may prevent the patient support apparatus 30 from potentially erratic movements (in examples of adjusting the positioning of portions of the patient support apparatus 30) that may discomfort the patient supported on the same. In each of the above embodiments, adjustment may be provided before the user provides the subsequent input confirm the desired action.

In certain embodiments, the speed with which the corresponding operation of the patient support apparatus 30 moves is based on the speed with which the user moves the pictorial representation 180 displayed on the touchscreen 114. For example, the controller 102 is configured to determine the speed with which the user moves the pictorial representation 180 displayed on the touchscreen 114 and interpolates by a correlation factor. The controller 102 may be configured to interpolate with one, two, or three or more correlation factors based on, for example, speed with which the user moves the pictorial representation 180 at the beginning, the middle, and the end of the motion. Alternatively, the controller 102 may average or otherwise manipulate variances in speed with which the user moves the pictorial representation 180 to determine and apply a singular correlation factor. The controller 102 provides a corresponding signal to control the operational devices 70-92 of the patient support apparatus 30, in this example the lift device 78, to move the patient support surface 42 at the appropriate speed. The correlation factor(s) may be selected by the user with the user touchscreen display 114.

A locking feature may be incorporated to prevent inadvertent movement of the patient support apparatus 30 as the user engages the pictorial representation 180 with the touchscreen display 114. The locking feature may comprise a "Lock" button LB displayed on the touchscreen display 114. FIG. 6 shows the button LB in a locked configuration. In the locked configuration, engagement with the pictorial representation 180 may not provide any corresponding movement of the pictorial representation 180 and/or the patient support apparatus 30. In one embodiment, the user slides the finger F when the pictorial representation 180 is in the locked configuration, the pictorial representation 180 remains static and provides no corresponding movement. The user may be required to actuate the button LB in order to engage the pictorial representation 180 and effectuate corresponding movement.

In some embodiments, indicia 124, 125, 126 may be visually displayed on the information output device 112 with the indicia 124, 125, 126 representative of the operational functions of the patient support apparatus 30. Providing the one or more instructions to the user comprises visually emphasizing the indicia 124, 125, 126 on the information output device in manners previously described.

As noted above, the subject patent application is related to U.S. Provisional Patent Application No. 62/525,359 filed on Jun. 27, 2017. In addition, the subject patent application is also related to: U.S. Provisional Patent Application No. 62/525,353 filed on Jun. 27, 2017 and its corresponding Non-Provisional patent application Ser. No. 16/020,068 filed on Jun. 27, 2018; U.S. Provisional Patent Application No. 62/525,363 filed on Jun. 27, 2017 and its corresponding Non-Provisional patent application Ser. No. 16/020,085 filed on Jun. 27, 2018; U.S. Provisional Patent Application No. 62/525,368 filed on Jun. 27, 2017 and its corresponding Non-Provisional Patent application Ser. No. 16/019,973 filed on Jun. 27, 2018; U.S. Provisional Patent Application No. 62/525,373 filed on Jun. 27, 2017 and its corresponding Non-Provisional Patent Application Ser. No. 16/020,003 filed on Jun. 27, 2018; and U.S. Provisional Patent Application No. 62/525,377 filed on Jun. 27, 2017 and its corresponding Non-Provisional patent application Ser. No. 16/019,986 filed on Jun. 27, 2018. The disclosures of each of the above-identified Provisional Patent Applications and corresponding Non-Provisional Patent Applications are each hereby incorporated by reference in their entirety.

It will be further appreciated that the terms "include," "includes," and "including" have the same meaning as the terms "comprise," "comprises," and "comprising."

Several embodiments have been discussed in the foregoing description. However, the embodiments discussed herein are not intended to be exhaustive or limit the invention to any particular form. The terminology which has been used is intended to be in the nature of words of description rather than of limitation. Many modifications and variations are possible in light of the above teachings and the invention may be practiced otherwise than as specifically described.

What is claimed is:

1. A patient support system comprising:

a patient support apparatus comprising a patient support surface configured to support a patient;

a touchscreen display comprising a user interface configured to receive input from a user and an information output device configured to provide a pictorial representation of the patient support apparatus with first and second selectable portions of the pictorial representation of the patient support apparatus, with the first selectable portion adapted to be engaged by the user with the touchscreen display and moved on the touchscreen display relative to one or more other portions of the pictorial representation of the patient support apparatus to control a first operational function of the patient support apparatus, and with the second selectable portion adapted to be engaged by the user with the touchscreen display and moved on the touchscreen display relative to the first selectable portion of the pictorial representation of the patient support apparatus to control a second operational function of the patient support apparatus; and a controller disposed in communication with the touchscreen display and configured to:

receive an input signal from the touchscreen display corresponding to one or more of:

movement, at a first input speed, of the first selectable portion of the pictorial representation of the patient support apparatus relative to the one or more other portions of the pictorial representation of the patient support apparatus occurring based on user engagement with the first selectable portion of the pictorial representation of the patient support apparatus on the touchscreen display; and movement, at a second input speed, of the second selectable portion of the pictorial representation of the patient support apparatus relative to the first selectable portion of the pictorial representation of the patient support apparatus occurring based on user engagement with the second selectable portion of the pictorial representation of the patient support apparatus on the touchscreen display, determine one or more of the first operational function and the second operational function of the patient support apparatus corresponding to the user engagement, and transmit a control signal for controlling one or more of:

the first operational function of the patient support apparatus at a first operation speed based on the first input speed defined by the user engagement with the first selectable portion of the pictorial representation of the patient support apparatus on the touchscreen display; and the second operational function of the patient support apparatus at a second operation speed based on the second input speed defined by the user engagement with the second selectable portion of the pictorial representation of the patient support apparatus on the touchscreen display;

wherein user engagement of the first selectable portion of the pictorial representation of the patient support apparatus on the touchscreen display defines a first input motion having a first beginning, a first middle, and a first end;

wherein the controller is further configured to determine the first operational speed based on interpolation of the first input speed by a first correlation factor including:

a first beginning correlation factor defined at the first beginning of the first input motion, a first middle correlation factor defined at the first middle of the first input motion, and a first end correlation factor defined at the first end of the first input motion;

wherein user engagement of the second selectable portion of the pictorial representation of the patient support apparatus on the touchscreen display defines a second input motion having a second beginning, a second middle, and a second end; and wherein the controller is further configured to determine the second operational speed based on interpolation of the second input speed by a second correlation factor including:

a second beginning correlation factor defined at the second beginning of the second input motion, a second middle correlation factor defined at the second middle of the second input motion, and a second end correlation factor defined at the second end of the second input motion.

2. The patient support system of claim 1, wherein the patient support apparatus further comprises:

a first operational device disposed in communication with the controller and configured to receive the control signal and to control the first operational function based on the control signal; and a second operational device disposed in communication with the controller and configured to receive the control signal and to control the second operational function based on the control signal.

3. The patient support system of claim 2, wherein the first operational device comprises a lift device; and wherein the second operational device comprises a deck adjustment device.

4. The patient support system of claim 1, wherein the touchscreen display is coupled to the patient support apparatus.

5. The patient support system of claim 1, wherein the touchscreen display is associated with a mobile device remote from the patient support apparatus.

6. The patient support system of claim 1, wherein the patient support apparatus includes:

a base arranged for movement along floor surfaces;

an intermediate frame; and a patient support deck operatively attached to the intermediate frame.

7. The patient support system of claim 6, wherein the first operational function is further defined as moving the intermediate frame relative to the base; and wherein the patient support apparatus further includes a lift device coupled between the base and the intermediate frame and having a lift actuator in communication with the controller to receive the control signal and to move the intermediate frame relative to the base based on the control signal.

8. The patient support system of claim 7, wherein the patient support deck includes a deck section arranged for articulation relative to the intermediate frame to at least partially adjust the patient support surface;

wherein the second operational function is further defined as articulating the deck section relative to the intermediate frame; and wherein the patient support apparatus further includes a deck adjustment device coupled between the intermediate frame and the deck section and having a deck actuator in communication with the controller to receive the control signal and to articulate the deck section relative to the intermediate frame based on the control signal.

9. The patient support system of claim 1, wherein the controller is further configured to transmit an output signal to provide an updated display of the pictorial representation on the touchscreen display depicting one or more of:

a moved first selectable portion of the pictorial representation of the patient support apparatus, and a moved second selectable portion of the pictorial representation of the patient support apparatus.

10. The patient support system of claim 9, wherein the user engagement includes an input to the touchscreen display to adjust one or more of:

the first selectable portion of the pictorial representation of the patient support apparatus, and the second selectable portion of the pictorial representation of the patient support apparatus; and wherein the controller is further configured to transmit the output signal to provide the updated display of the pictorial representation comprising one or more of:

the first selectable portion of the pictorial representation of the patient support apparatus moved based on the input, and the second selectable portion of the pictorial representation of the patient support apparatus moved based on the input.

11. The patient support system of claim 9, wherein the touchscreen display is further configured to display a virtual locking feature selectable by the user.

12. The patient support system of claim 11, wherein the controller is further configured to, in response to user selection of the virtual locking feature, transmit a disable signal to disable controlling one or more of:

the first operational function of the patient support apparatus, and the second operational function of the patient support apparatus; and wherein the controller is further configured to transmit the output signal to provide the updated display of the pictorial representation comprising the pictorial representation of the patient support apparatus in response to user input to the touchscreen display following user selection of the virtual locking feature.

13. The patient support system of claim 9, wherein the user engagement includes one or more of:

a first selection on the pictorial representation of a first desired component of the patient support apparatus corresponding to the first selectable portion of the pictorial representation of the patient support apparatus, and a second selection on the pictorial representation of a second desired component of the patient support apparatus corresponding to the second selectable portion of the pictorial representation of the patient support apparatus;

wherein the controller is further configured to transmit the output signal to visually emphasize the first desired component in response to selection of the first selectable portion of the pictorial representation of the patient support apparatus on the touchscreen display; and wherein the controller is further configured to transmit the output signal to visually emphasize the second desired component in response to selection of the second selectable portion of the pictorial representation of the patient support apparatus on the touchscreen display.

14. The patient support system of claim 9, wherein the user engagement includes an input to the touchscreen display of one or more of:

a first desired action of the first operational function of the patient support apparatus, and a second desired action of the second operational function of the patient support apparatus; and wherein the controller is further configured to transmit the output signal to simulate, on the touchscreen display, one or more of:

the first desired action, and the second desired action.

15. The patient support system of claim 1, wherein the user interface is further configured to receive a search input comprising a search query;

wherein the information output device is further configured to provide a search result and an instruction to the user with the search result related to a searched operational function of the patient support apparatus;

wherein the controller is further configured to:

receive a search input signal from the user interface based on the search query, determine the search result corresponding to the searched operational function of the patient support apparatus responsive to the search query, transmit a result output signal to provide the search result to the user with the information output device, and receive a user selection from the search result with the user interface.

16. The patient support system of claim 15, wherein the information output device is configured to display a virtual keyboard having virtual keys; and wherein the user interface is configured receive the search query from the user actuating the virtual keys of the virtual keyboard.

17. The patient support system of claim 15, wherein the information output device is configured to display a search field;

wherein the user interface is configured to receive virtual freeform writing from a stylus within the search field; and wherein the information output device is further configured to display letters and/or numbers comprising the search query corresponding to the virtual freeform writing.

* * * * *